(12) United States Patent
Lee et al.

(10) Patent No.: US 8,242,159 B2
(45) Date of Patent: Aug. 14, 2012

(54) 1,3-DIHYDRO-5-ISOBENZOFURANCARBONITRILE DERIVATIVES AND PHARMACEUTICAL COMPOSITION THEREOF FOR THE TREATMENT OF PREMATURE EJACULATION

(75) Inventors: Yeong Geon Lee, Gunpo-si (KR); Soo-Jung Choi, Seoul (KR); Tae-Kyung Kang, Seoul (KR); Mi-Jeong Seo, Yongin-si (KR); Chang-Yong Shin, Seoul (KR); Kyung-Seok Lee, Yongin-si (KR); Gook-Jun Ahn, Yongin-si (KR); Seul-Min Choi, Suwon-si (KR); Yong-Duck Kim, Suwon-si (KR); Dong-Hwan Kim, Seoul (KR); Kyung-Koo Kang, Suwon-si (KR); Hyun-Joo Shim, Yongin-si (KR); Dong-Sung Kim, Seoul (KR); Byoung-Ok Ahn, Yongin-si (KR); Moo-Hi Yoo, Seoul (KR)

(73) Assignee: Dong-A Pharmaceutical. Co., Ltd, Seoul (KR)

( * ) Notice: Subject to any disclaimer, the term of this patent is extended or adjusted under 35 U.S.C. 154(b) by 111 days.

(21) Appl. No.: 12/739,870

(22) PCT Filed: Oct. 31, 2008

(86) PCT No.: PCT/KR2008/006445
§ 371 (c)(1),
(2), (4) Date: Apr. 26, 2010

(87) PCT Pub. No.: WO2009/057974
PCT Pub. Date: May 7, 2009

(65) Prior Publication Data
US 2010/0240725 A1    Sep. 23, 2010

(30) Foreign Application Priority Data

Nov. 2, 2007 (KR) .................. 10-2007-0111783
Oct. 27, 2008 (KR) .................. 10-2008-0105439

(51) Int. Cl.
*A61K 31/415* (2006.01)
*A61K 31/4164* (2006.01)
*A61K 31/38* (2006.01)
*A61K 31/34* (2006.01)
*C07D 233/00* (2006.01)
*C07D 231/00* (2006.01)
*C07D 409/00* (2006.01)
*C07D 307/02* (2006.01)

(52) U.S. Cl. ........ 514/397; 514/406; 514/444; 514/469; 548/311.4; 548/364.4; 549/60; 549/467

(58) Field of Classification Search .................. 514/397, 514/406, 444, 469; 548/311.4, 364.4; 549/60, 549/467
See application file for complete search history.

(56) References Cited

U.S. PATENT DOCUMENTS
4,136,193 A    1/1979    Bogeso et al.

FOREIGN PATENT DOCUMENTS
WO    03/042202 A1    5/2003

OTHER PUBLICATIONS

[Kim, Dong Sung. Synthesis and Biological Properties of New 5-Cyano-1,1-disubstituted Phthalans for the Treatment of Premature Ejaculation. Bull. Korean Chem. Soc. 29(10), (2008), 1946-1950.].*
Atmaca, et al., "The efficacy of citalopram in the treatment of premature ejaculation: a placebo-controlled study", International Journal of Impotence Research, 2002, 14, 502-505.
Eildal, et al., "From the selective serotonin transporter inhibitor citalopram to the selective norepinephrine transporter inhibitor talopram: Synthesis and structure-activity relationship studies", Journal of Medicinal Chemistry, 2008, 51 (10):3045-3048.

* cited by examiner

*Primary Examiner* — Joseph K. McKane
*Assistant Examiner* — Samantha Shterengarts
(74) *Attorney, Agent, or Firm* — Lucas & Mercanti, LLP

(57) ABSTRACT

Disclosed herein are novel 1,3-dihydro-5-isobenzofurancarbonitrile derivatives represented by Formula 1, or pharmaceutically acceptable salts thereof. Also disclosed is a pharmaceutical composition for treating or preventing premature ejaculation including the compound. The 1,3-dihydro-5-isobenzofurancarbonitrile derivatives have a short half-life and inhibit the ejaculation process by selectively inhibiting serotonin reuptake via a serotonin reuptake transporter present in a presynaptic neuron. Thus, the compounds are useful in the treatment and prevention of premature ejaculation.

18 Claims, No Drawings

1,3-DIHYDRO-5-ISOBENZOFURANCARBONITRILE DERIVATIVES AND PHARMACEUTICAL COMPOSITION THEREOF FOR THE TREATMENT OF PREMATURE EJACULATION

CROSS-REFERENCE TO RELATED APPLICATIONS

This application is a 371 of PCT/KR2008/006445 filed on Oct. 31, 2008, which claims the benefit of Korean Patent Application Nos. 10-2007-0111783 filed on Nov. 2, 2007, and 10-2008-0105439 filed on Oct. 27, 2008, the contents of each of which are incorporated herein by reference.

TECHNICAL FIELD

The present invention relates to 1,3-dihydro-5-isobenzofurancarbonitrile derivatives represented by Formula 1, below, or pharmaceutically acceptable salts thereof and a pharmaceutical composition for treating or preventing premature ejaculation comprising the same as an effective ingredient.

[Formula 1]

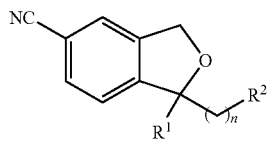

BACKGROUND ART

There are various concepts with premature ejaculation. There lacks a universally acknowledged definition of premature ejaculation. According to DSM-IV-TR (Diagnostic and Statistical Manual of Mental Disorders, Fourth Edition, Text Revision), it defines premature ejaculation as the persistent or recurrent onset of orgasm and ejaculation with minimal sexual stimulation before, during, or shortly after penetration and before the person wishes it.

Premature ejaculation is recognized to be the most common male sexual disorder, affecting approximately 30% of men. This prevalence rate is three times higher than that of erectile dysfunction (Int J Impot Res 2005 17:39-57). Erectile dysfunction is common in middle-aged men as well as in older men, whereas premature ejaculation occurs in men of all ages and has a deleterious impact on quality of life. Premature ejaculation is generally classified as either primary or secondary. Primary form applies to men who have had the condition since they became capable of functioning sexually (i.e., post-puberty). Primary premature ejaculation (PE) is associated with changes of neurotransmitters, which are involved in a variety of psychological actions. Secondary PE is considered when an individual has been able to control his ejaculation and faced no problem earlier but later is unable to do so due to mental stress, erectile dysfunction, prostatitis, urethritis or drug administration.

The two main causes contributing to premature ejaculation are biological and psychogenic factors. Biological factors include penile hypersensitivity, hyperexcitability of ejaculatory reflex, increased sexual arousability, endocrinopathy, genetic predisposition, and 5-HT receptor dysfunction. Psychogenic risk factors include anxiety, early sexual experiences, ejaculatory control techniques, and psychodynamics (J Sex Med 2004 1:58-65).

The ejaculatory process is mediated by a complex interplay of neurotransmitters, such as 5-hydroxytryptamine (5-HT) and dopamine. Cholinergic, adrenergic, GA-BAnergic and oxytocinergic neurons have also been shown to be involved in the regulation of ejaculation. Of these, 5-HT has been known to play a major role in the regulation of ejaculation (Urology 2003 61:623-628). The overall role of serotonin (5-HT) on ejaculation has been shown to be inhibitory (Physiol Behav 2004 83:291-307). 5-HT released at L3-L5 spinal segments from terminals of axons descending from the rostral region of the paragigantocellular nucleus (nPGi) in the brainstem exerts an inhibitory role on ejaculation (Exp Brain Res 1992 88:313-320). Also, ejaculation is inhibited when 5-HT is released from serotonergic neurons in the medial preoptic area (MPOA), which is a hypothalamic brain area. (Eur J Pharmacol 1992 210:121-129). Serotonin is released from presynaptic neurons and acts on receptors on postsynaptic neurons in which 5-HT2C receptor mediates the effects of serotonin on ejaculation. Presynaptic 5-HT1B and somatodendritic 5-HT 1A autoreceptors induce a negative feedback control over 5-HT release and prevent over-stimulation of postsynaptic 5-HT receptors to inhibit ejaculation. Then, 5-HT molecules present in the synapse are taken up again back into the presynaptic neuron via 5-HT transporter, which is located on the cell bodies of the presynaptic neuron. In this way, 5-HT is implicated in the control of ejaculation (European Urology 2006 50:454-466).

There are non-drug treatment and drug treatment for premature ejaculation.

Non-drug treatment for premature ejaculation is equally said behavioral therapies. The most popular methods are the squeeze technique developed by Masters & Johnson (1970) and the stop-start technique developed by Semans (1956). However, there are problems with the two techniques in terms that they are time-consuming and require the proper participation of his partner, leading to difficulty in practice and low success rates (Contemp Urol 2001 13:51-59).

No drug is approved by the American FDA for the treatment of premature ejaculation. However, many studies have shown that topical anesthetics, off-label use of antidepressants, and the like are effective to treat premature ejaculation. The most commonly used topical anesthetic cream to desensitize the head of the penis is EMLA cream or spray that contains lidocaine and prilocaine. The lidocaine-prilocaine formulation has been shown to be in part effective in premature ejaculation and to improve sexual satisfaction when applied 30 minutes before sexual intercourse, but causes decreased penile sensation and vaginal numbness in a female partner (Int J Impot Res 2003 15:277-281). A domestically developed SS cream, which is prepared with an extract from nine Chinese herbal medicines, significantly increases intra vaginal ejaculation latency time (IVELT) in a clinical trial, but it is currently not marketed due to its low effectiveness and side effects including local burning and pain (Yonsei Med J 1997 38:91-95).

Tricyclic antidepressants (TCAs) and selective serotonin reuptake inhibitors (SSRIs) are currently used off-label. TCAs are less selective for inhibition of serotonin reuptake and have more side effects than SSRIs (Contemp Urol 2001 13:51-59).

SSRIs, such as Fluoxetine, paroxetine, sertraline, citalopram and fluvoxamine, have been shown to be effective in treating premature ejaculation. In particular, U.S. Pat. No. 4,136,193 discloses anti-depressive 1-dimethylaminopropyl- 1-phenylphthalans, which comprise the citalopram compound that is similar to compounds according to the present invention. When various doses and administration schemes were tested, continuous daily administration of SSRI over a 2-wk period prolonged IVELT by 3-10 minutes and was thus more effective in premature ejaculation than a single dosing before intercourse (J Urol 1998 159:1935-1938).

However, the long-term use of SSRIs increases the incidence of side effects such as vomiting, dry mouth, drowsiness, reduced libido and an ejaculation (J Sex Marital Ther 1999 25:89-101). With respect to effectiveness, SSRIs have another decisive drawback of having no indication for their use in premature ejaculation treatment. Moreover, SSRIs are intended for chronic use rather than on-demand use because they have a long half-life and a long Tmax, which is the time to maximal plasma concentration, and it takes a long time for SSRIs to exert their therapeutic effects or efficacies, and these are difficult to predict.

When SSRI drugs are used in combination with monoamine oxidase inhibitors such as lithium, sumatriptan and tryptophan, there is an increased risk of serotonin syndrome with side effects including fever, delirium, coma, sweating and dizziness (N Eng J Med 2005 352:1112-1120).

In this regard, the inventors of the present application conducted intensive and thorough research in order to develop a compound that has a good ejaculation-delaying effect, an about three times shorter half-life and better safety and is thus suitable for on-demand use in premature ejaculation treatment. The research resulted in the findings that novel 1,3-dihydro-5-isobenzofurancarbonitrile derivatives or pharmaceutically acceptable salts thereof have a good ejaculation-delaying effect with a short half-life, thereby leading to the present invention.

DISCLOSURE OF INVENTION

Technical Problem

It is therefore an object of the present invention to provide novel 1,3-dihydro-5-isobenzofurancarbonitrile derivatives or pharmaceutically acceptable salts thereof and a method of preparing the same.

It is another object of the present invention to provide a pharmaceutical composition for treating or preventing premature ejaculation, the composition having a short half-life and a good ejaculation-delaying effect.

Technical Solution

In order to accomplish the above objects, the present invention provides novel 1,3-dihydro-5-isobenzofurancarbonitrile derivatives or pharmaceutically acceptable salts thereof.

Advantageous Effects

In accordance with the present invention, the 1,3-dihydro-5-isobenzofurancarbonitrile derivatives have a short half-life and inhibit the ejaculation process by selectively inhibiting serotonin reuptake via a serotonin reuptake transporter present in a presynaptic neuron. Thus, the present invention is useful in the treatment or prevention of premature ejaculation.

BEST MODE FOR CARRYING OUT THE INVENTION

Hereinafter, the present invention will be described in detail.

In one aspect, the present invention provides 1,3-dihydro-5-isobenzofurancarbonitrile derivatives, represented by Formula 1, below, or pharmaceutically acceptable salts thereof:

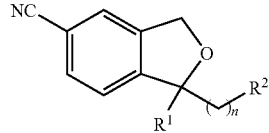

[Formula 1]

The present invention comprises following derivates.

1) A derivative represented by Formula 1 or a pharmaceutically acceptable salt thereof:
$R^1$ is a substituted or unsubstituted phenyl; or heterocyclyl selected from pyridinyl, isoxazolyl, thiazolyl, pyrimidinyl, indanyl, benzthiazolyl, pyrazolyl, thiadiazolyl, oxazolyl, piperidinyl, morpholinyl, imidazolyl, pyrrolidinyl, thienyl, triazolyl, pyrrolyl and furyl;
$R^2$ is $C_1$-$C_6$ dialkylamino, or a substituted or unsubstituted heterocyclyl selected from pyridinyl, isoxazolyl, thiazolyl, pyrimidinyl, indanyl, benzthiazolyl, pyrazolyl, thiadiazolyl, oxazolyl, piperidinyl, morpholinyl, imidazolyl, pyrrolidinyl, thienyl, triazolyl, pyrrolyl and furyl; and
n is an integer from 1 to 3.

2) A derivative represented by Formula 1 or a pharmaceutically acceptable salt thereof:
$R^1$ is a substituted or unsubstituted phenyl; or heterocyclyl selected from pyridinyl, isoxazolyl, thiazolyl, pyrimidinyl, indanyl, benzthiazolyl, pyrazolyl, thiadiazolyl, oxazolyl, piperidinyl, morpholinyl, imidazolyl, pyrrolidinyl, thienyl, triazolyl, pyrrolyl and furyl; and in case that the $R^1$ contains a substituent, the substituent is $C_1$-$C_6$ alkyl, $C_1$-$C_6$ alkyloxy, $C_1$-$C_6$ dialkylamine or halogen;
$R^2$ is $C_1$-$C_6$ dialkylamino, or a substituted or unsubstituted heterocyclyl selected from pyridinyl, isoxazolyl, thiazolyl, pyrimidinyl, indanyl, benzthiazolyl, pyrazolyl, thiadiazolyl, oxazolyl, piperidinyl, morpholinyl, imidazolyl, pyrrolidinyl, thienyl, triazolyl, pyrrolyl and furyl; and
n is an integer from 1 to 3.

3) A derivative represented by Formula 1 or a pharmaceutically acceptable salt thereof:
$R^1$ is a substituted or unsubstituted phenyl; or heterocyclyl selected from pyridinyl, isoxazolyl, thiazolyl, pyrimidinyl, indanyl, benzthiazolyl, pyrazolyl, thiadiazolyl, oxazolyl, piperidinyl, morpholinyl, imidazolyl, pyrrolidinyl, thienyl, triazolyl, pyrrolyl and furyl;
$R^2$ is $C_1$-$C_6$ dialkylamino, pyrazolyl, or imidazolyl; and
n is an integer from 1 to 3.

4) A derivative represented by Formula 1 or a pharmaceutically acceptable salt thereof:
$R^1$ is phenyl substituted with $C_1$-$C_6$ alkyloxy;
$R^2$ is $C_1$-$C_6$ dialkylamino, or a substituted or unsubstituted heterocyclyl selected from pyridinyl, isoxazolyl, thiazolyl, pyrimidinyl, indanyl, benzthiazolyl, pyrazolyl, thiadiazolyl, oxazolyl, piperidinyl, morpholinyl, imidazolyl, pyrrolidinyl, thienyl, triazolyl, pyrrolyl and furyl; and
n is an integer from 1 to 3.

In a preferred embodiment of the invention, the $R^1$ is methoxyphenyl;
the $R^2$ is $C_1$-$C_6$ dialkylamino, or a substituted or unsubstituted heterocyclyl selected from pyridinyl, isoxazolyl, thiazolyl, pyrimidinyl, indanyl, benzthiazolyl, pyrazolyl, thiadiazolyl, oxazolyl, piperidinyl, morpholinyl, imidazolyl, pyrrolidinyl, thienyl, triazolyl, pyrrolyl and furyl; and
the n is an integer from 1 to 3.

In a more preferred embodiment of the invention, the $R^1$ is methoxyphenyl;
the $R^2$ is dimethylamino, pyrazolyl, or imidazolyl; and
the n is an integer from 1 to 3.

5) A derivative represented by Formula 1 or a pharmaceutically acceptable salt thereof:
$R^1$ is unsubstituted phenyl or phenyl substituted with $C_1$-$C_6$ alkyl;
$R^2$ is $C_1$-$C_6$ dialkylamino, or a substituted or unsubstituted heterocyclyl selected from pyridinyl, isoxazolyl, thiazolyl, pyrimidinyl, indanyl, benzthiazolyl, pyrazolyl, thiadiazolyl, oxazolyl, piperidinyl, morpholinyl, imidazolyl, pyrrolidinyl, thienyl, triazolyl, pyrrolyl and furyl; and
n is an integer from 1 to 3.

In a preferred embodiment of the invention, the $R^1$ is unsubstituted phenyl or tolyl;
the $R^2$ is $C_1$-$C_6$ dialkylamino, or a substituted or unsubstituted heterocyclyl selected from pyridinyl, isoxazolyl, thiazolyl, pyrimidinyl, indanyl, benzthiazolyl, pyrazolyl, thiadiazolyl, oxazolyl, piperidinyl, morpholinyl, imidazolyl, pyrrolidinyl, thienyl, triazolyl, pyrrolyl and furyl; and
the n is an integer from 1 to 3.

In a more preferred embodiment of the invention, the $R^1$ is unsubstituted phenyl or tolyl;
the $R^2$ is $C_1$-$C_6$ dialkylamino, pyrazolyl, or imidazolyl; and
the n is an integer from 1 to 3.

6) A derivative represented by Formula 1 or a pharmaceutically acceptable salt thereof:
$R^1$ is phenyl substituted with $C_1$-$C_6$ dialkylamino;
$R^2$ is $C_1$-$C_6$ dialkylamino, or a substituted or unsubstituted heterocyclyl selected from pyridinyl, isoxazolyl, thiazolyl, pyrimidinyl, indanyl, benzthiazolyl, pyrazolyl, thiadiazolyl, oxazolyl, piperidinyl, morpholinyl, imidazolyl, pyrrolidinyl, thienyl, triazolyl, pyrrolyl and furyl; and
n is an integer from 1 to 3.

In a preferred embodiment of the invention, the $R^1$ is dimethylaminophenyl;
the $R^2$ is $C_1$-$C_6$ dialkylamino, or a substituted or unsubstituted heterocyclyl selected from pyridinyl, isoxazolyl, thiazolyl, pyrimidinyl, indanyl, benzthiazolyl, pyrazolyl, thiadiazolyl, oxazolyl, piperidinyl, morpholinyl, imidazolyl, pyrrolidinyl, thienyl, triazolyl, pyrrolyl and furyl; and
the n is an integer from 1 to 3.

In a more preferred embodiment of the invention, the $R^1$ is dimethylaminophenyl;
the $R^2$ is dimethylamino, pyrazolyl, or imidazolyl; and
the n is an integer from 1 to 3.

7) A derivative represented by Formula 1 or a pharmaceutically acceptable salt thereof:
$R^1$ is thienyl;
$R^2$ is $C_1$-$C_6$ dialkylamino, or a substituted or unsubstituted heterocyclyl selected from pyridinyl, isoxazolyl, thiazolyl, pyrimidinyl, indanyl, benzthiazolyl, pyrazolyl, thiadiazolyl, oxazolyl, piperidinyl, morpholinyl, imidazolyl, pyrrolidinyl, thienyl, triazolyl, pyrrolyl and furyl; and
the n is an integer from 1 to 3.

In a preferred embodiment of the invention, the $R^1$ is thienyl;
the $R^2$ is dimethylamino, pyrazolyl, or imidazolyl; and
the n is an integer from 1 to 3.

8) A derivative represented by Formula 1 or a pharmaceutically acceptable salt thereof:
$R^1$ is phenyl substituted halogen;
$R^2$ is a substituted or unsubstituted heterocyclyl selected from pyridinyl, isoxazolyl, thiazolyl, pyrimidinyl, indanyl, benzthiazolyl, pyrazolyl, thiadiazolyl, oxazolyl, piperidinyl, morpholinyl, imidazolyl, pyrrolidinyl, thienyl, triazolyl, pyrrolyl and furyl; and
n is an integer from 1 to 3.

In a preferred embodiment of the invention, the $R^1$ is phenyl substituted halogen;
the $R^2$ is pyrazolyl or imidazolyl; and
the n is an integer from 1 to 3.

The pharmaceutically acceptable salts of the compounds of Formula 1 include acid addition salts formed with an inorganic acid or an organic acid. Examples of inorganic acids include hydrochloric acid, hydrobromic acid, hydroiodic acid, sulfuric acid, and phosphoric acid. Examples of organic acids include p-toluenesulfonic acid, methanesulfonic acid, oxalic acid, p-bromophenylsulfonic acid, carbonic acid, succinic acid, citric acid, benzoic acid, and acetic acid. Examples of such pharmaceutically acceptable salts include sulfate, pyrosulfate, bisulfate, sulfite, bisulfite, phosphate, mono-hydrogenphosphate, dihydrogenphosphate, metaphosphate, pyrophosphate, bromide, iodide, acetate, propionate, decanoate, caprylate, acrylate, formate, chloride, dichloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycollate, tartrate, methanesulfonate, propanesulfonate, naphthalene-1-sulfonate, naphthalene-2-sulfonate, and mandelate. Preferred pharmaceutically acceptable acid addition salts are those formed with inorganic acids, such as hydrochloric acid and hydrobromic acid, and those formed with organic acids, such as oxalic acid and maleic acid.

Particularly preferred examples of the compound of Formula 1 according to the present invention include the following:

1-{3-(dimethylamino)propyl}-1-(4-methoxyphenyl)-1,3-dihydro-5-isobenzofurancarbonitrile;
1-{3-(dimethylamino)propyl}-1-(4-methoxyphenyl)-1,3-dihydro-5-isobenzofurancarbonitrile oxalate;
1-{3-(dimethylamino)propyl}-1-(4-methoxyphenyl)-1,3-dihydro-5-isobenzofurancarbonitrile hydrochloride;
1-{3-(imidazole-1-yl)propyl}-1-(4-methoxyphenyl)-1,3-dihydro-5-isobenzofurancarbonitrile;
1-{3-(imidazole-1-yl)propyl}-1-(4-methoxyphenyl)-1,3-dihydro-5-isobenzofurancarbonitrile hydrochloride;
1-{2-(imidazole-1-yl)ethyl}-1-(4-methoxyphenyl)-1,3-dihydro-5-isobenzofurancarbonitrile;
1-{2-(imidazole-1-yl)ethyl}-1-(4-methoxyphenyl)-1,3-dihydro-5-isobenzofurancarbonitrile hydrochloride;
1-(4-methoxyphenyl)-1-{3-(pyrazole-1-yl)propyl}-1,3-dihydro-5-isobenzofurancarbonitrile;
1-(4-methoxyphenyl)-1-{3-(pyrazole-1-yl)propyl}-1,3-dihydro-5-isobenzofurancarbonitrile hydrochloride;
1-(4-methoxyphenyl)-1-{2-(pyrazole-1-yl)ethyl}-1,3-dihydro-5-isobenzofurancarbonitrile;
1-(4-methoxyphenyl)-1-{2-(pyrazole-1-yl)ethyl}-1,3-dihydro-5-isobenzofurancarbonitrile hydrochloride;
1-{3-(dimethylamino)propyl}-1-phenyl-1,3-dihydro-5-isobenzofurancarbonitrile;
1-{3-(dimethylamino)propyl}-1-phenyl-1,3-dihydro-5-isobenzofurancarbonitrile hydrochloride;
1-{2-(dimethylamino)ethyl}-1-phenyl-1,3-dihydro-5-isobenzofurancarbonitrile;
1-{2-(dimethylamino)ethyl}-1-phenyl-1,3-dihydro-5-isobenzofurancarbonitrile hydrochloride;

1-{3-(imidazole-1-yl)propyl}-1-phenyl-1,3-dihydro-5-isobenzofurancarbonitrile;
1-{3-(imidazole-1-yl)propyl}-1-phenyl-1,3-dihydro-5-isobenzofurancarbonitrile hydrochloride;
1-{2-(imidazole-1-yl)ethyl}-1-phenyl-1,3-dihydro-5-isobenzofurancarbonitrile;
1-{2-(imidazole-1-yl)ethyl}-1-phenyl-1,3-dihydro-5-isobenzofurancarbonitrile hydrochloride;
1-phenyl-1-{2-(pyrazole-1-yl)ethyl}-1,3-dihydro-5-isobenzofurancarbonitrile;
1-phenyl-1-{2-(pyrazole-1-yl)ethyl}-1,3-dihydro-5-isobenzofurancarbonitrile hydrochloride;
1-{3-(dimethylamino)propyl}-1-(4-tolyl)-1,3-dihydro-5-isobenzofurancarbonitrile;
1-{3-(dimethylamino)propyl}-1-(4-tolyl)-1,3-dihydro-5-isobenzofurancarbonitrile hydrochloride;
1-{2-(dimethylamino)ethyl}-1-(4-tolyl)-1,3-dihydro-5-isobenzofurancarbonitrile;
1-{2-(dimethylamino)ethyl}-1-(4-tolyl)-1,3-dihydro-5-isobenzofurancarbonitrile hydrochloride;
1-{3-(imidazole-1-yl)propyl}-1-(4-tolyl)-1,3-dihydro-5-isobenzofurancartonitrile;
1-{3-(imidazole-1-yl)propyl}-1-(4-tolyl)-1,3-dihydro-5-isobenzofurancartonitrile hydrochloride;
1-{2-(imidazole-1-yl)ethyl}-1-(4-tolyl)-1,3-dihydro-5-isobenzofurancarbonitrile;
1-{2-(imidazole-1-yl)ethyl}-1-(4-tolyl)-1,3-dihydro-5-isobenzofurancarbonitrile hydrochloride;
1-{3-(pyrazole-1-yl)propyl}-1-(4-tolyl)-1,3-dihydro-5-isobenzofurancartonitrile;
1-{3-(pyrazole-1-yl)propyl}-1-(4-tolyl)-1,3-dihydro-5-isobenzofurancartonitrile hydrochloride;
1-{2-(pyrazole-1-yl)ethyl}-1-(4-tolyl)-1,3-dihydro-5-isobenzofurancarbonitrile;
1-{2-(pyrazole-1-yl)ethyl}-1-(4-tolyl)-1,3-dihydro-5-isobenzofurancarbonitrile hydrochloride;
1-(4-dimethylaminophenyl)-1-{3-(dimethylamino)propyl}-1,3-dihydro-5-isobenzofurancarbonitrile;
1-(4-dimethylaminophenyl)-1-{3-(dimethylamino)propyl}-1,3-dihydro-5-isobenzofurancarbonitrile oxalate;
1-(4-dimethylaminophenyl)-1-{3-(dimethylamino)propyl}-1,3-dihydro-5-isobenzofurancarbonitrile hydrochloride;
1-(4-dimethylaminophenyl)-1-{3-(imidazole-1-yl)propyl}-1,3-dihydro-5-isobenzofurancarbonitrile;
1-(4-dimethylaminophenyl)-1-{3-(imidazole-1-yl)propyl}-1,3-dihydro-5-isobenzofurancarbonitrile hydrochloride;
1-{3-(dimethylamino)propyl}-1-(2-thienyl)-1,3-dihydro-5-isobenzofurancarbonitrile;
1-{3-(dimethylamino)propyl}-1-(2-thienyl)-1,3-dihydro-5-isobenzofurancarbonitrile oxalate;
1-{3-(dimethylamino)propyl}-1-(2-thienyl)-1,3-dihydro-5-isobenzofurancarbonitrile hydrochloride;
1-{2-(dimethylamino)ethyl}-1-(2-thienyl)-1,3-dihydro-5-isobenzofurancarbonitrile;
1-{2-(dimethylamino)ethyl}-1-(2-thienyl)-1,3-dihydro-5-isobenzofurancarbonitrile hydrochloride;
1-{3-(imidazole-1-yl)propyl}-1-(2-thienyl)-1,3-dihydro-5-isobenzofurancartonitrile;
1-{3-(imidazole-1-yl)propyl}-1-(2-thienyl)-1,3-dihydro-5-isobenzofurancartonitrile oxalate;
1-{3-(imidazole-1-yl)propyl}-1-(2-thienyl)-1,3-dihydro-5-isobenzofurancarbonitrile hydrochloride;
1-{2-(imidazole-1-yl)ethyl}-1-(2-thienyl)-1,3-dihydro-5-isobenzofurancarbonitrile;
1-{2-(imidazole-1-yl)ethyl}-1-(2-thienyl)-1,3-dihydro-5-isobenzofurancarbonitrile hydrochloride;
1-{3-(pyrazole-1-yl)propyl}-1-(2-thienyl)-1,3-dihydro-5-isobenzofurancartonitrile;
1-{3-(pyrazole-1-yl)propyl}-1-(2-thienyl)-1,3-dihydro-5-isobenzofurancartonitrile hydrochloride;
1-{2-(pyrazole-1-yl)ethyl}-1-(2-thienyl)-1,3-dihydro-5-isobenzofurancarbonitrile;
1-{2-(pyrazole-1-yl)ethyl}-1-(2-thienyl)-1,3-dihydro-5-isobenzofurancarbonitrile hydrochloride;
1-(4-fluorophenyl)-1-{3-(imidazole-1-yl)propyl}-1,3-dihydro-5-isobenzofurancarbonitrile;
1-(4-fluorophenyl)-1-{3-(imidazole-1-yl)propyl}-1,3-dihydro-5-isobenzofurancarbonitrile hydrochloride;
1-(4-fluorophenyl)-1-{2-(imidazole-1-yl)ethyl}-1,3-dihydro-5-isobenzofurancartonitrile;
1-(4-fluorophenyl)-1-{2-(imidazole-1-yl)ethyl}-1,3-dihydro-5-isobenzofurancartonitrile hydrochloride;
1-(4-fluorophenyl)-1-{3-(pyrazole-1-yl)propyl}-1,3-dihydro-5-isobenzofurancarbonitrile;
1-(4-fluorophenyl)-1-{3-(pyrazole-1-yl)propyl}-1,3-dihydro-5-isobenzofurancarbonitrile hydrochloride;
1-(4-fluorophenyl)-1-{2-(pyrazole-1-yl)ethyl}-1,3-dihydro-5-isobenzofurancartonitrile;
1-(4-fluorophenyl)-1-{2-(pyrazole-1-yl)ethyl}-1,3-dihydro-5-isobenzofurancartonitrile hydrochloride;
1-(4-chlorophenyl)-1-{3-(imidazole-1-yl)propyl}-1,3-dihydro-5-isobenzofurancarbonitrile;
1-(4-chlorophenyl)-1-{3-(imidazole-1-yl)propyl}-1,3-dihydro-5-isobenzofurancarbonitrile hydrochloride;
1-(4-chlorophenyl)-1-{2-(imidazole-1-yl)ethyl}-1,3-dihydro-5-isobenzofurancarbonitrile;
1-(4-chlorophenyl)-1-{2-(imidazole-1-yl)ethyl}-1,3-dihydro-5-isobenzofurancarbonitrile hydrochloride;
1-(4-chlorophenyl)-1-{3-(pyrazole-1-yl)propyl}-1,3-dihydro-5-is obenzofurancarbonitrile;
1-(4-chlorophenyl)-1-{3-(pyrazole-1-yl)propyl}-1,3-dihydro-5-is obenzofurancarbonitrile hydrochloride;
1-(4-chlorophenyl)-1-{2-(pyrazole-1-yl)ethyl}-1,3-dihydro-5-isobenzofurancarbonitrile; and
1-(4-chlorophenyl)-1-{2-(pyrazole-1-yl)ethyl}-1,3-dihydro-5-isobenzofurancarbonitrile hydrochloride.

In another aspect, the present invention provides a method of preparing the compound represented by Formula 1 or a pharmaceutically acceptable salt thereof.

The present method is shown in Reaction Scheme 1, below.

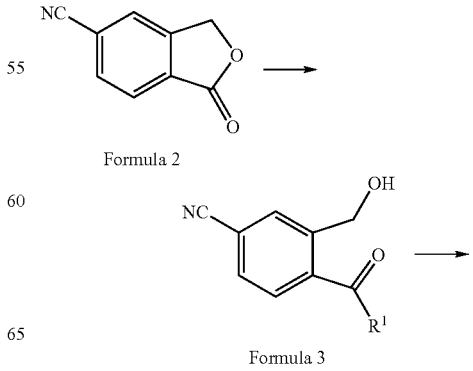

[Reaction Scheme 1]

Formula 2

Formula 3

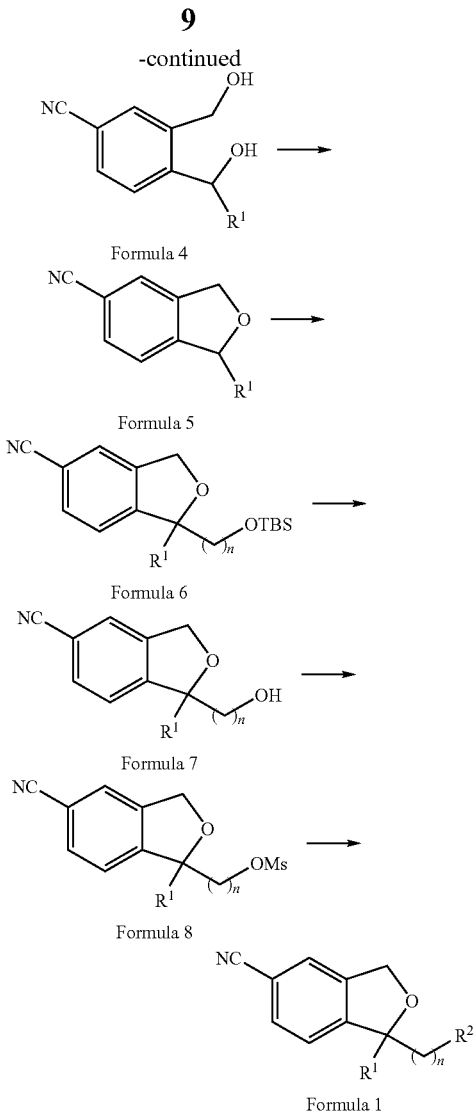

Formula 4

Formula 5

Formula 6

Formula 7

Formula 8

Formula 1

The compound of Formula 1 according to the present invention, as shown in Reaction Scheme 1, may be prepared through a series of steps from a 5-cyanophthalimide compound of Formula 2. In the Reaction Scheme 1, $R^1$, $R^2$ and n are the same as defined in Formula 1.

The method comprises:

1) preparing a compound of Formula 3 by reacting 5-cyanophthalimide compound of Formula 2 with $R^1$MgBr (step 1);

2) preparing a compound of Formula 4 by reduction reaction of the compound of Formula 3 (step 2);

3) preparing a compound of Formula 5 by cyclization reaction of the compound of Formula 4 (step 3);

4) preparing a compound of Formula 6 by introducing an alkyl group into position 1 of the compound of Formula 5 (step 4);

5) preparing a compound of Formula 7 by deprotecting the compound of Formula 6 (step 5);

6) preparing a compound of Formula 8 by reacting the compound of Formula 7 with methanesulfonylchloride (step 6);

7) preparing a compound of Formula 1 by substitution reaction of the compound of Formula 8 with a $R^2$ group and saltation (with HCl or oxalic acid) (step 7).

Each step of the method will be described in further detail below.

The 5-cyanophthalimide of Formula 2 used as a starting compound at step 1 may be prepared using a known method (Il Farmaco 2001, 56, 715). At step 1, a Grignard's reaction is carried out with $R^1$MgBr. Examples of solvents useful in the reaction include tetrahydrofuran, 1,4-dioxane, diethylether, dimethoxyethane, and dichloromethane. Dichloromethane is preferred. The reaction is carried out at a temperature between 0° C. and room temperature for 10 to 20 hours.

At step 2, the reduction reaction may be carried out using sodium borohydride as a reducing reagent. The reducing reagent is used in an amount ranging from 0.5 to 3 equivalents, and preferably 2 equivalents.

At step 3, the cyclization reaction of Formula 4 is carried out under an acidic condition. Examples of useful acids include hydrochloric acid, sulfuric acid, and phosphoric acid, phosphoric acid being preferred.

At step 4, bases such as lithium diisopropyl amine, sodium hydride, n-butylamine, sodium methoxide and potassium t-butoxide may be used. Sodium hydride is preferred. Examples of suitable solvents include dimethylsulfoxide, dimethylformamide, N-methylpyrrolidine-2-one, tetrahydrofurane, and 1,4-dioxane. Dimethylsulfoxide is preferred. The reaction is carried out at 50° C. to 110° C. for 12 to 36 hours.

At step 5, a protecting group of Formula 6 may be removed using hydrogen fluoride, potassium fluoride, tetrabutylammonium fluoride, hydrochloric acid, sulfuric acid, or the like. Tetrabutylammonium fluoride is preferred. The deprotection reaction is carried out using tetrahydrofurane as a solvent at room temperature for about 1 hour.

At step 6, the leaving group may be introduced into the compound of Formula 8 using methanesulfonylchloride, p-toluenesulfonylchloride, trichloromethanesulfonylchloride, or the like. Methanesulfonylchloride is preferred. The reaction is carried out in the presence of dichloromethane as a solvent at 0° C. for about 1 hour.

At step 7, bases suitable for use in the $R^2$ substitution reaction include carbonates, such as sodium carbonate, calcium carbonate, potassium carbonate and cesium carbonate, and hydroxides, such as sodium hydroxide, calcium hydroxide and potassium hydroxide. Potassium carbonate is preferred. Examples of solvents suitable for use in the reaction include dimethylsulfoxide, dimethylformamide, N-methylpyrrolidine-2-one, tetrahydrofurane, and 1,4-dioxane, and dimethylformamide being preferred. The reaction is carried out at 50° C. to 110° C. for 12 to 36 hours so as to obtain the target compound of Formula 1, a 1,3-dihydro-5-isobenzofurancarbonitrile derivative. Optionally, the compound is reacted with hydrochloric acid or oxalic acid for 10 to 60 minutes so as to obtain the 1,3-dihydro-5-isobenzofurancarbonitrile derivative in a salt form of hydrochloride or oxalate.

In a further aspect, the present invention provides a pharmaceutical composition for treating or preventing premature ejaculation comprising the novel 1,3-dihydro-5-isobenzofurancarbonitrile derivative represented by Formula 1, below, or a pharmaceutically acceptable salt thereof as an effective ingredient, the composition having a short half-life and a good inhibitory effect on ejaculation.

The 1,3-dihydro-5-isobenzofurancarbonitrile derivatives according to the present invention have a short half-life and inhibit the ejaculation process by selectively inhibiting serotonin reuptake via a serotonin reuptake transporter present in a presynaptic neuron. The present compounds are thus useful in the treatment and prevention of premature ejaculation.

The pharmaceutical composition, comprising the novel 1,3-dihydro-5-isobenzofurancarbonitrile derivative according to the present invention or a pharmaceutically acceptable salt thereof as an effective ingredient, may be used in general pharmaceutical dosage forms. That is, the compounds of the present invention may be administered in a wide variety of oral and parenteral dosage forms upon clinical application, oral administration being preferred in the present invention. A formulation may be prepared with generally used diluents or excipients, such as fillers, thickeners, binders, humectants, disintegrators and surfactants.

Solid formulations for oral administration may include tablets, pills, powders, granules and capsules, and are prepared by mixing the 1,3-dihydro-5-isobenzofurancarbonitrile derivative or a pharmaceutically acceptable salt thereof with one or more excipients, such as starch, calcium carbonate, sucrose, lactose and gelatin. Also, the solid formulations may include, in addition to a simple excipient, a lubricant such as magnesium stearate or talc. Liquid formulations for oral administration may include suspensions, internal solutions, emulsions and syrups. The liquid formulations may include, in addition to commonly used simple diluents, such as water and liquid paraffin, various excipients, which are exemplified by humectants, sweeteners, aromatics and preservatives. Formulations for parenteral administration may include sterile aqueous solutions, non-aqueous solutions, suspensions, emulsions, lyophilized preparations, and suppositories. Non-aqueous solutions and suspensions may be prepared with propylene glycol, polyethylene glycol, vegetable oils such as olive oil, and injectable esters such as ethyl oleate. As a base for suppositories, Witepsol, macrogol, Tween 61, cacao oil, laurin oil and glycerinated gelatin may be used.

The dosage of the pharmaceutical composition of the present invention, comprising the 1,3-dihydro-5-isobenzofurancarbonitrile derivative or a pharmaceutically acceptable salt thereof as an effective ingredient, may vary depending on the patient's weight, age, gender and diet, the time and mode of administration, excretion rates, and the severity of illness. The present composition may be administered in an effective amount ranging from 0.1 to 1,000 mg, and preferably in a daily dosage of 10 to 50 mg. The daily dosage may be taken in a single dose or may be divided into several doses.

Mode for the Invention

A better understanding of the present invention may be obtained through the following examples which are set forth to illustrate, but are not to be construed as the limit of the present invention.

The molecular structure of the present compound of Formula 1 was identified through infrared spectroscopy, UV-visible spectroscopy, nuclear magnetic resonance spectroscopy, mass spectroscopy, and comparison of calculated and experimental values of elementary analysis of a representative compound.

EXAMPLE 1

Preparation of 1-(4-methoxyphenyl)-1-{3-(dimethylamino)propyl}-1,3-dihydro-5-isobenzofurancarbonitrile (compound 1)

Step 1: Preparation of 3-hydroxymethyl-4-(4-methoxybenzoyl)benzonitrile 20.0 g (125.6 mmol) of 5-cyanophthalimide was dissolved in 200 ml of anhydrous dichloromethane. The solution was cooled to −78° C., and 188 ml of 4-methoxyphenylmagnesium bromide (1 M in THF, 188 mmol) was added dropwise. The mixture was raised to room temperature and stirred for 16 hrs, followed by addition of a saturated ammonium chloride solution. An organic layer was dried over anhydrous magnesium sulfate, and filtered. The solvent was evaporated under reduced pressure, thereby yielding a yellow compound, represented by Formula 3. The compound thus obtained was used in the next reaction without further purification.

$^1$H NMR(400 MHz, CDCl$_3$): 3.89(s, 3H), 4.60(d, J=6.0 Hz, 2H), 6.95(d, J=7.2 Hz, 2H), 7.48(d, J=7.6 Hz, 1H), 7.65 (d, J=7.6 Hz, 1H), 7.75(d, J=7.2 Hz, 2H), 7.86(s, 1H).

Step 2: Preparation of 4-{hydroxy(4-methoxyphenyl)methyl}-3-(hydroxymethyl)benzonitrile 33.6 g (125.6 mmol) of the 3-hydroxymethyl-4-(4-methoxybenzoyl)benzonitrile prepared in step 1 was dissolved in 200 ml of dichloromethane and 100 ml of methanol. The solution was cooled to 0° C., and 95 g (251.1 mmol) of sodium borohydride was slowly added.

The mixture was raised to room temperature and stirred for 3 hrs, followed by addition of a saturated ammonium chloride solution. An organic layer was dried over anhydrous magnesium sulfate, and filtered. The solvent was evaporated under reduced pressure, thereby yielding a yellow compound represented by Formula 4. The compound thus obtained was used in the next reaction without further purification.

$^1$H NMR(400 MHz, DMSO-d$_6$): 3.70(s, 3H), 4.28(dd, J=14.8 Hz, 5.4 Hz, 1H), 4.57(dd, J=14.8 Hz, 5.4 Hz, 1H), 5.37(t, J=5.4 Hz. 1H), 5.83(d, J=4.2 Hz, 1H), 5.94(d, J=4.2 Hz, 1H), 6.85(d, J=8.8 Hz, 2H), 7.15(d, J=8.8 Hz, 2H), 6.69-7.73(m, 2H), 7.75(s, 1H).

Step 3: Preparation of 1-(4-methoxyphenyl)-1,3-dihydro-5-isobenzofurancarbonitrile 33.82 g (125.6 mmol) of the 4-{hydroxy(4-methoxyphenyl)methyl}-3-(hydroxymethyl)benzonitrile prepared in step 2 was dissolved in 150 ml of ethylacetate, and 150 ml of a 85% aqueous solution of phosphoric acid was added at room temperature. The mixture was raised to 80° C. and stirred for 3 hrs. The reaction mixture was then cooled again to room temperature, and washed with water and saturated NaCl solution. An organic layer was dried over anhydrous magnesium sulfate, and filtered. The solvent was evaporated under reduced pressure. The residue was treated with 2-propanol to afford 18.0 g of a white solid (yield: 57%).

$^1$H NMR(400 MHz, CDCl$_3$): 2.73(s, 3H), 5.10(d, J=13.0 Hz, 1H), 5.27(dd, J=13.0 Hz, 1H), 6.17(s, 1H), 6.91(d, J=8.4 Hz, 2H), 7.17-7.24(m, 3H), 7.70(d, J=8.0 Hz, 1H), 7.87(s, 1H).

Step 4: Preparation of 1-(3-tert-butyldimethylsilyloxypropyl)-1-(4-methoxyphenyl)-1,3-dihydro-5-isobenzofurancarbonitrile 23.0 g (91.3 mmol) of the 1-(4-methoxyphenyl)-1,3-dihydro-5-isobenzofurancarbonitrile prepared in step 3 was dissolved in 200 ml of dimethylsulfoxide. 5.5 g (137.0 mmol) of sodium hydride was slowly added to the solution at room temperature. The solution was stirred for 0.5 hr. Then, to the mixture, 34.7 g (137.0 mmol) of bromo-1-(tert-butyldimethylsilyl)propane was added. The resulting mixture was raised to 80° C., stirred for 12 hrs, and cooled again to room temperature. The reaction mixture was mixed with water, extracted with ethylacetate, and washed with water and saturated NaCl solution. An organic layer was dried over anhydrous magnesium sulfate, and filtered. The solvent was evaporated under reduced pressure. The residue was purified using column chromatography to afford 34.1 g (yield: 88%) of the pale yellow target compound.

$^1$H NMR(400 MHz, CDCl$_3$): 0.06(s, 6H), 0.89(s, 9H), 1.34(m, 1H), 1.52(m, 1H), 1.95(m, 1H), 2.21(m, 1H), 3.57(t,

J=6.2 Hz, 1H), 3.65(t, J=6.2 Hz, 1H), 3.76(s, 3H), 5.16(m, 2H), 6.85(d, J=8.2 Hz, 2H), 7.33-7.35(m, 3H), 7.49(s, 1H), 7.57(d, J=8.0 Hz, 1H).

Step 5: Preparation of 1-(3-hydroxypropyl)-1-(4-methoxyphenyl)-1,3-dihydro-5-isobenzofurancarbonitrile 34.1 g (80.8 mmol) of the 1-(3-tert-butyldimethylsilyloxypropyl)-1-(4-methoxyphenyl)-1,3-dihydro-5-isobenzofurancarbonitrile prepared in step 4 was dissolved in 200 ml of tetrahydrofuran. 121.1 ml (121.1 mmol) of 1 M tetrabutylammonium fluoride tetrahydrofuran was added dropwise to the solution at room temperature, and the mixture was stirred for 2 hrs. The reaction mixture was diluted in ethylacetate, and washed with water and saturated NaCl solution. An organic layer was dried over anhydrous magnesium sulfate, and filtered. The solvent was evaporated under reduced pressure. The residue was purified using column chromatography to afford 15.0 g of the pale yellow target compound (yield: 60%).

$^1$H NMR(400 MHz, CDCl$_3$): 1.46(m, 1H), 1.55(m, 1H), 2.18(m, 1H), 2.30(m, 1H), 3.59(m, 2H), 3.76(s, 3H), 5.15(m, 2H), 6.83(d, J=8.8 Hz, 2H), 7.31-7.38(m, 3H), 7.48(s, 1H), 7.57(d, J=8.0 Hz, 1H).

Step 6: Preparation of 1-(3-methanesulfonyloxypropyl)-1-(4-methoxyphenyl)-1,3-dihydro-5-isobenzofurancarbonitrile 15.0 g (48.5 mmol) of the 1-(3-hydroxypropyl)-1-(4-methoxyphenyl)-1,3-dihydro-5-isobenzofurancarbonitrile prepared in step 5 was dissolved in 200 ml of dichloromethane, and 7.4 g (727 mmol) of triethylamine and 6.7 g (58.2 mol) of methanesulfonylchloride were added dropwise at 0° C. The solution was then stirred for 1 hr. The reaction mixture was washed with water and saturated NaCl solution. An organic layer was dried over anhydrous magnesium sulfate, and filtered. The solvent was evaporated under reduced pressure to afford 18.2 g of the yellow target compound (yield: 79%). The compound thus obtained was used in the next reaction without further purification.

$^1$H NMR(400 MHz, CDCl$_3$): 1.64(m, 1H), 1.71(m, 1H), 2.19(m, 1H), 2.30(m, 1H), 2.94(s, 3H), 3.76(s, 3H), 4.20(m, 2H), 5.15(m, 2H), 6.84(d, J=8.8 Hz, 2H), 7.32(d, J=8.8 Hz, 2H), 7.37(d, J=8.0 Hz, 1H), 7.47(s, 1H), 7.57(d, J=8.0 Hz, 1H).

Step 7: Preparation of 1-{3-(dimethylamino)propyl}-1-(4-methoxyphenyl)-1,3-dihydro-5-isobenzofurancarbonitrile (compound 1)

18.2 g (47.0 mmol) of the 1-(3-methanesulfonyloxypropyl)-1-(4-methoxyphenyl)-1,3-dihydro-5-isobenzofurancarbonitrile prepared in step 6 was dissolved in 300 ml of dimethylformimide, and 13.0 g (94.0 mmol) of potassium carbonate and 94.0 ml (188.0 mmol) of 2 M dimethylamine in tetrahydrofuran were added at room temperature. The solution temperature was then raised to 80° C. and stirred for 12 hrs. The reaction mixture was diluted in ethylacetate and washed with water and saturated NaCl solution. A resulting organic layer was dried over anhydrous magnesium sulfate, and filtered. After the solvent was evaporated under reduced pressure, the residue was purified with column chromatography to afford 8.3 g (yield: 53%) of a pale yellow compound, 1-(4-methoxyphenyl)-1-{3-(dimethylamino)propyl}-1,3-dihydro-5-isobenzofurancarbonitrile.

$^1$H NMR(400 MHz, CDCl$_3$): 1.42(m, 1H), 1.55(m, 1H), 2.11-2.31(m, 7H), 2.42(m, 2H), 3.75(s, 3H), 4.20(m, 2H), 5.15(m, 2H), 6.83(d, J=8.8 Hz, 2H), 7.34(d, J=8.8 Hz, 2H), 7.40(d, J=7.8 Hz, 1H), 7.46(s, 1H), 7.59(d, J=7.8 Hz, 1H).

EXAMPLE 2

Preparation of 1-{3-(dimethylamino)propyl}-1-(4-methoxyphenyl)-1,3-dihydro-5-isobenzofurancarbonitrile oxalate 8.3 g (24.7 mmol) of the 1-{3-(dimethylamino)propyl}-1-(4-methoxyphenyl)-1,3-dihydro-5-isobenzofurancarbonitrile prepared in Example 1 was dissolved in 85 ml of ethanol, and 3.4 g (27.2 mmol) of oxalic acid was slowly added at room temperature. The solution was stirred at room temperature for 0.5 hr, and it was cooled to 0° C. and further stirred for 1 hr. The solution was filtered to recover the precipitate. The precipitate was washed with hexane and dried to afford 7.1 g of the target compound as a white solid (yield: 67%).

$^1$H NMR(400 MHz, DMSO-d$_6$): 1.41(m, 1H), 1.49(m, 1H), 2.18(m, 2H), 2.61(s, 6H), 2.95(t, J=7.8 Hz, 2H), 3.65(s, 3H), 5.19(d, J=13.2 Hz, 1H), 5.12(d, J=13.2 Hz, 1H), 6.88(d, J=8.8 Hz, 2H), 7.42(d, J=8.8 Hz, 2H), 7.68(d, J=7.6 Hz, 1H), 7.77(d, J=7.6 Hz, 1H), 7.78(s, 1H).

$^{13}$C NMR(100 MHz, DMSO-d$_6$): 19.3, 36.9, 42.2, 55.0, 56.6, 70.9, 90.2, 110.2, 113.6, 118.6, 122.8, 125.5, 125.9, 131.8, 135.5, 139.6, 149.2, 158.1, 164.1.

EXAMPLE 3

Preparation of 1-{3-(dimethylamino)propyl}-1-(4-methoxyphenyl)-1,3-dihydro-5-isobenzofurancarbonitrile hydrochloride 8.3 g (24.7 mmol) of the 1-{3-(dimethylamino)propyl}-1-(4-methoxyphenyl)-1,3-dihydro-5-isobenzofurancarbonitrile prepared in Example 1 was dissolved in 50 ml of dichloromethane, and 24.7 ml (494 mmol) of 2 M hydrochloric acid in diethyl ether was added dropwise at room temperature. The mixture was then stirred for 0.5 hr. After the solution was discarded, the precipitate was washed with diethylether and dried to afford 8.7 g of the pale yellow target compound (yield: 95%).

$^1$H NMR(400 MHz, DMSO-d$_6$): 1.45(m, 1H), 1.56(m, 1H), 2.24(t, J=7.6 Hz, 2H), 2.59(s, 3H), 2.61(s, 3H), 2.98(m, 2H), 3.70(s, 3H), 5.12(d, J=13.2 Hz, 1H), 5.21(d, J=13.2 Hz, 1H), 6.87(d, J=8.4 Hz, 2H), 7.44(d, J=8.4 Hz, 2H), 7.70(d, J=7.6 Hz, 1H), 7.77(d, J=7.6 Hz, 1H), 7.78(s, 1H), 10.62(brs, 1H).

$^{13}$C NMR(100 MHz, DMSO-d$_6$): 19.0, 36.9, 41.8, 41.9, 55.0, 56.3, 70.6, 90.2, 110.2, 113.6, 118.6, 122.9, 125.5, 125.8, 131.7, 135.6, 139.6, 149.2, 158.1.

According to the same method as described in Examples 1 to 3, the compounds of Examples 4 to 68, below, were prepared by using a Grignard reagent, amine and acid corresponding to each substituent of the compounds of Examples 4 to 68.

EXAMPLE 4

Preparation of 1-{3-(imidazole-1-yl)propyl}-1-(4-methoxyphenyl)-1,3-dihydro-5-isobenzofurancarbonitrile $^1$H NMR(400 MHz, CDCl$_3$): 1.69(m, 1H), 1.78(m, 1H), 1.98(m, 1H), 2.14(m, 1H), 3.72(s, 3H), 3.94(t, J=7.0 Hz, 2H), 5.13(m, 2H), 6.78-6.85(m, 3H), 7.05 (s, 1H), 7.23-7.29(m, 3H), 7.45(s, 1H), 7.54-7.57(m, 2H).

EXAMPLE 5

Preparation of 1-{13-(imidazole-1-yl)propyl}-1-(4-methoxyphenyl)-1,3-dihydro-5-isobenzofurancarbonitrile hydrochloride $^1$H NMR(400 MHz, DMSO-$d_6$): 1.67(m, 1H), 1.71(m, 1H), 2.14(m, 2H), 3.69(s, 3H), 4.17(t, J=7.0 Hz, 2H), 5.09(d, J=13.4 Hz, 1H), 5.17(d, J=13.4 Hz, 1H), 6.86(d, J=8.8 Hz, 2H), 7.39(d, J=8.8 Hz, 2H), 7.61-7.67(m, 2H), 7.73-7.77(m, 3H) 9.18(s, 1H).
$^{13}$C NMR(100 MHz, DMSO-$d_6$): 24.9, 36.7, 48.3, 55.0, 70.9, 90.1, 110.2, 113.6, 118.0, 119.5, 121.7, 122.9, 125.4, 125.8, 131.7, 134.9, 135.5, 139.6, 149.1, 158.1.

EXAMPLE 6

Preparation of 1-{2-(imidazole-1-yl)ethyl}-1-(4-methoxyphenyl)-1,3-dihydro-5-isobenzofurancarbonitrile $^1$H NMR(400 MHz, CDCl$_3$): 2.62(m, 1H), 2.77(m, 1H), 3.77(s, 3H), 4.00(t, J=7.8 Hz, 2H), 5.17(m, 2H), 6.84-6.88(m, 3H), 7.05(s, 1H), 7.36(d, J=7.2 Hz, 2H), 7.45(d, J=8.0 Hz, 1H), 7.50(s, 1H), 7.59(d, J=8.0 Hz, 1H), 7.92(s, 1H).

EXAMPLE 7

Preparation of 1-{2-(imidazole-1-yl)ethyl}-1-(4-methoxyphenyl)-1,3-dihydro-5-isobenzofurancarbonitrile hydrochloride $^1$H NMR(400 MHz, DMSO-$d_6$): 2.85(m, 2H), 3.71(s, 3H), 4.10(m, 2H), 5.13(d, J=13.4 Hz, 1H), 5.22(d, J=13.4 Hz, 1H), 6.89(d, J=8.2 Hz, 2H), 7.44(d, J=8.2 Hz, 2H), 7.56(s, 1H), 7.65-7.75(m, 3H), 7.79(s, 1H), 895(s, 1H), 14.23(brs, 1H).
13C NMR(100 MHz, DMSO-d6): 40.1, 44.7, 55.1, 71.1, 89.1, 110.4, 113.7, 118.5, 119.3, 121.8, 122.8, 125.5, 125.7, 131.8, 135.0, 135.1, 139.3, 148.2, 158.2.

EXAMPLE 8

Preparation of 1-(4-methoxyphenyl)-1-{3-(pyrazole-1-yl)propyl}-1,3-dihydro-5-isobenzofurancarbonitrile $^1$H NMR(400 MHz, CDCl$_3$): 1.74(m, 1H), 1.85(m, 1H), 2.03(m, 1H), 2.15(m, 1H), 3.74(s, 3H), 4.09(m, 2H), 5.12(m, 2H), 6.20(s, 1H), 6.34(s, 1H), 6.81(d, J=7.6 Hz, 2H), 7.23-7.29(m, 3H), 7.45(s, 1H), 7.53(d, J=7.6 Hz, 1H), 7.61(s, 1H).

EXAMPLE 9

Preparation of 1-(4-methoxyphenyl)-1-{3-(pyrazole-1-yl)propyl}-1,3-dihydro-5-isobenzofurancarbonitrile hydrochloride $^1$H NMR(400 MHz, DMSO-$d_6$): 1.54(m, 1H), 1.63(m, 1H), 2.09(m, 2H), 3.69(s, 3H), 4.04(t, J=7.0 Hz, 2H), 5.07(d, J=13.6 Hz, 1H), 5.14(d, J=13.6 Hz, 1H), 6.16(m, 1H), 6.29(m, 1H), 6.85(d, J=8.8 Hz, 2H), 7.36(d, J=8.8 Hz, 2H), 7.59-7.75(m, 4H).

$^{13}$C NMR(100 MHz, DMSO-$d_6$): 25.3, 37.2, 50.9, 55.1, 70.9, 90.3, 105.1, 110.2, 113.6, 118.7, 122.9, 125.5, 125.9, 130.3, 131.8, 135.7, 137.6, 139.7, 149.1, 158.1.

EXAMPLE 10

Preparation of 1-(4-methoxyphenyl)-1-{2-(pyrazole-1-yl)ethyl}-1,3-dihydro-5-isobenzofurancarbonitrile $^1$H NMR(400 MHz, CDCl$_3$): 2.78(m, 2H), 4.14(m, 2H), 5.18(m, 2H), 6.10(s, 1H), 6.84(d, J=8.8 Hz, 2H), 7.16(s, 1H), 7.34-7.37(m, 3H), 7.44-7.46(m, 2H), 7.52(d, J=8.0 Hz, 1H).

EXAMPLE 11

Preparation of 1-(4-methoxyphenyl)-1-{2-(pyrazole-1-yl)ethyl}-1,3-dihydro-5-isobenzofurancarbonitrile hydrochloride $^1$H NMR(400 MHz, DMSO-$d_6$): 2.72(m, 2H), 3.71(s, 3H), 3.97(m, 2H), 5.15(d, J=13.4 Hz, 1H), 5.25(d, J=13.4 Hz, 1H), 6.11(s, 1H), 6.88(d, J=7.6 Hz, 2H), 7.32(s, 1H), 7.47(d, J=7.6 Hz, 2H), 7.59(s, 1H), 7.68-7.74(m, 2H), 7.78(s, 1H), 11.82 (brs, 1H).
$^{13}$C NMR(100 MHz, DMSO-$d_6$): 40.4, 47.1, 55.1, 71.2, 89.2, 105.0, 110.3, 113.7, 118.6, 122.9, 125.5, 125.8, 130.2, 131.8, 135.3, 137.7, 139.4, 148.6, 158.2.

EXAMPLE 12

Preparation of 1-{3-(dimethylamino)propyl}-1-phenyl-1,3-dihydro-5-isobenzofurancarbonitrile $^1$H NMR(400 MHz, CDCl$_3$): 1.40(m, 1H), 1.52(m, 1H), 2.10-2.48(m, 10H), 5.17(m, 2H), 7.22-7.33(m, 4H), 7.43-7.47(m, 3H), 7.57(d, J=8.0 Hz, 1H).

EXAMPLE 13

Preparation of 1-{3-(dimethylamino)propyl}-1-phenyl-1,3-dihydro-5-isobenzofurancarbonitrile hydrochloride $^1$H NMR(400 MHz, DMSO-$d_6$): 1.43(m, 1H), 1.52(m, 1H), 2.25(m, 2H), 2.56(s, 6H), 2.96(m, 2H), 5.16(m, 2H), 7.20(m, 1H), 7.29(m, 2H), 7.53(m, 2H), 7.65-7.85(m, 3H), 10.69(brs, 1H).
$^{13}$C NMR(100 MHz, DMSO-$d_6$): 18.8, 36.8, 41.7, 41.8, 56.1, 71.0, 90.2, 110.1, 118.3, 122.8, 124.3, 125.3, 126.8, 128.0, 131.6, 139.3, 143.3, 148.5.

EXAMPLE 14: Preparation of 1-{2-(dimethylamino)ethyl}-1-phenyl-1,3-dihydro-5-isobenzofurancarbonitrile $^1$H NMR(400 MHz, CDCl$_3$): 2.22(s, 6H), 2.29(m, 2H), 2.41(m, 2H), 5.14(m, 2H), 7.23-7.42(m, 6H), 7.47(s, 1H), 7.57(d, J=7.8 Hz, 1H).

EXAMPLE 15

Preparation of 1-{2-(dimethylamino)ethyl}-1-phenyl-1,3-dihydro-5-isobenzofurancarbonitrile hydrochloride $^1$H NMR(400 MHz, DMSO-$d_6$): 2.66-2.70(m, 4H), 2.71(s, 3H), 2.87(s, 3H), 5.17(d, J=13.4 Hz, 1H), 5.24(d, J=13.4

1H), 7.27(m, 1H), 7.36(m, 2H), 7.57(d, J=7.6 Hz, 2H), 7.77-7.82(m, 2H), 7.94(s, 1H), 10.75(brs, 1H).
$^{13}$C NMR(100 MHz, DMSO-d$_6$): 35.0, 42.8, 42.9, 53.4, 72.2, 89.9, 111.5, 119.3, 123.9, 125.3, 126.6, 128.3, 129.3, 132.9, 140.2, 143.6, 148.7.

EXAMPLE 16

Preparation of 1-{3-(imidazole-1-yl)propyl}-1-phenyl-1,3-dihydro-5-isobenzofurancarbonitrile $^1$H NMR(400 MHz, CDCl$_3$): 1.68(m, 1H), 1.70(m, 1H), 2.03(m, 1H), 2.16(m, 1H), 3.91(m, 2H), 5.28(m, 2H), 6.80(s, 1H), 7.02(s, 1H), 7.23-7.39(m, 6H), 7.47(s, 1H), 7.59(d, J=8.0 Hz, 1H), 7.99(s, 1H).

EXAMPLE 17

Preparation of 1-{3-(imidazole-1-yl)propyl}-1-phenyl-1,3-dihydro-5-isobenzofurancarbonitrile hydrochloride $^1$H NMR(400 MHz, DMSO-d$_6$): 1.62(m, 1H), 1.70(m, 1H), 2.17(t, J=7.4 Hz, 2H), 4.15(t, J=7.2 Hz, 2H), 5.13(d, J=13.4 Hz, 1H), 5.19(d, J=13.4 Hz, 1H), 7.21-7.34(m, 3H), 7.51(d, J=8.0 Hz, 2H), 7.64(s, 1H), 7.71-7.79(m, 4H), 9.08(s, 1H), 14.44(brs, 1H).
$^{13}$C NMR(100 MHz, DMSO-d$_6$): 24.1, 36.0, 47.9, 70.6, 89.3, 109.2, 117.5, 118.9, 121.3, 122.4, 123.7, 124.8, 126.2, 127.5, 131.1, 134.3, 138.5, 142.5, 147.6.

EXAMPLE 18

Preparation of 1-{2-(imidazole-1-yl)ethyl}-1-phenyl-1,3-dihydro-5-isobenzofurancarbonitrile $^1$H NMR(400 MHz, CDCl$_3$): 2.69(m, 1H), 2.79(m, 1H), 4.02(m, 2H), 5.16(d, J=12.8 Hz, 1H), 5.23(d, J=12.8 Hz, 1H), 6.86(s, 1H), 7.08(s, 1H), 7.32(d, J=8.4 Hz, 2H), 7.42-7.44(m, 3H), 7.51(s, 1H), 7.54(d, J=7.8 Hz, 1H), 7.61(d, J=7.8 Hz, 1H), 8.29(s, 1H).

EXAMPLE 19

Preparation of 1-{2-(imidazole-1-yl)ethyl}-1-phenyl-1,3-dihydro-5-isobenzofurancarbonitrile hydrochloride $^1$H NMR(400 MHz, DMSO-d$_6$): 2.80(m, 1H), 2.93(m, 1H), 4.22(m, 2H), 5.17(d, J=13.4 Hz, 1H), 5.26(d, J=13.4 Hz, 1H), 7.41(d, J=8.4 Hz, 2H), 7.56-7.61(m, 3H), 7.68-7.78(m, 4H), 7.82(s, 1H), 9.00(s, 1H), 14.80(brs, 1H).
$^{13}$C NMR(100 MHz, DMSO-d$_6$): 38.1, 44.5, 71.3, 88.9, 110.7, 118.4, 119.2, 121.8, 122.9, 125.6, 126.4, 128.3, 131.9, 132.0, 135.0, 139.3, 142.3, 147.3.

EXAMPLE 20

Preparation of 1-phenyl-1-{2-(pyrazole-1-yl)ethyl}-1,3-dihydro-5-isobenzofurancarbonitrile $^1$H NMR(400 MHz, CDCl$_3$): 2.74(t, J=6.8 Hz, 2H), 4.10(t, J=6.8 Hz, 2H), 5.15(d, J=13.0 Hz, 1H), 5.23(d, J=13.0 Hz, 1H), 6.06(s, 1H), 7.12(s, 1H), 7.27(d, J=8.0 Hz, 2H), 7.32-7.40(m, 5H), 7.46(s, 1H), 7.51(d, J=7.6 Hz, 1H).

EXAMPLE 21

Preparation of 1-phenyl-1-{2-(pyrazole-1-yl)ethyl}-1,3-dihydro-5-isobenzofurancarbonitrile hydrochloride $^1$H NMR(400 MHz, DMSO-d$_6$): 2.75(m, 2H), 3.99(t, J=7.6 Hz, 2H), 5.18(d, J=13.4 Hz, 1H), 5.28(d, J=13.4 Hz, 1H), 6.11(s, 1H), 7.25(m, 1H), 7.32-7.36(m, 3H), 7.58-7.60(m, 3H), 7.74-7.78(m, 3H), 12.00(brs, 1H).

EXAMPLE 22

Preparation of 1-{3-(dimethylamino)propyl}-1-(4-tolyl)-1,3-dihydro-5-isobenzofurancarbonitrile $^1$H NMR(400 MHz, CDCl$_3$): 1.51(m, 1H), 1.64(m, 1H), 2.17(m, 1H), 2.29(s, 3H), 2.32(m, 1H), 2.37(s, 6H), 2.56(s, 2H), 5.14(d, J=13.2 Hz, 1H), 5.19(d, J=13.2 Hz, 1H), 7.12(d, J=7.6 Hz, 2H), 7.33(d, J=7.6 Hz, 2H), 7.43-7.46(m, 2H), 7.56(d, J=8.4 Hz, 1H).

EXAMPLE 23

Preparation of 1-{3-(dimethylamino)propyl}-1-(4-tolyl)-1,3-dihydro-5-isobenzofurancarbonitrile hydrochloride $^1$H NMR(400 MHz, DMSO-d$_6$): 1.46(m, 1H), 1.55(m, 1H), 2.14-2.31(m, 5H), 2.59(s, 6H), 2.99(m, 2H), 5.12(d, J=13.0 Hz, 1H), 5.21(d, J=13.0 Hz, 1H), 7.12(d, J=7.6 Hz, 2H), 7.42(d, J=7.6 Hz, 2H), 7.70-7.77(m, 3H), 10.82(brs, 1H).
$^{13}$C NMR(100 MHz, DMSO-d$_6$): 19.0, 20.5, 36.9, 41.8, 56.2, 71.0, 90.4, 110.2, 118.6, 122.9, 124.5, 125.4, 128.8, 131.7, 136.1, 139.5, 140.6, 149.1.

EXAMPLE 24

Preparation of 1-{2-(dimethylamino)ethyl}-1-(4-tolyl)-1,3-dihydro-5-isobenzofurancarbonitrile $^1$H NMR(400 MHz, CDCl$_3$): 2.26(s, 6H), 2.29(s, 3H), 2.32-2.50(m, 4H), 5.13(d, J=12.8 Hz, 1H), 5.17(d, J=12.8 Hz, 1H), 7.13(d, J=8.0 Hz, 2H), 7.32(d, J=8.0 Hz, 2H), 7.43(d, J=8.0 Hz, 1H), 7.47(s, 1H), 7.57(d, J=8.0 Hz, 1H).

EXAMPLE 25

Preparation of 1-{2-(dimethylamino)ethyl}-1-(4-tolyl)-1,3-dihydro-5-isobenzofurancarbonitrile hydrochloride $^1$H NMR(400 MHz, DMSO-d$_6$): 2.24(s, 3H), 2.67(s, 6H), 2.70-2.87(m, 4H), 5.15(d, J=13.2 Hz, 1H), 5.23(d, J=13.2 Hz, 1H), 7.16(d, J=8.4 Hz, 2H), 7.45(d, J=8.4 Hz, 2H), 7.74-7.81(m, 3H), 11.13(brs, 1H).
$^{13}$C NMR(100 MHz, DMSO-d$_6$): 20.6, 34.1, 41.8, 52.5, 71.1, 89.0, 110.6, 118.5, 122.9, 124.4, 125.6, 129.0, 131.9, 136.6, 139.3, 139.7, 148.2.

EXAMPLE 26

Preparation of 1-{3-(imidazole-1-yl)propyl}-1-(4-tolyl)-1,3-dihydro-5-isobenzofurancarbonitrile $^1$H NMR(400 MHz, CDCl$_3$): 1.72(m, 1H), 1.77(m, 1H), 1.99(m, 1H), 2.16(m, 1H), 2.29(s, 3H), 3.97(t, J=7.0 Hz, 2H), 5.14(m, 2H), 6.84(s, 1H), 7.07(s, 1H), 7.11(d, J=8.4 Hz, 2H), 7.25(d, J=8.4 Hz, 2H), 7.32(d, J=7.8 Hz, 1H), 7.46(s, 1H), 7.55(d, J=7.8 Hz, 1H), 7.69(s, 1H).

EXAMPLE 27

Preparation of 1-{3-(imidazole-1-yl)propyl}-1-(4-tolyl)-1,3-dihydro-5-isobenzofurancarbonitrile hydrochloride $^1$H NMR(400 MHz, DMSO-$d_6$): 1.61(m, 1H), 1.70(m, 1H), 2.16(m, 2H), 2.20(s, 3H), 4.19(m, 2H), 5.09(d, J=13.0 Hz, 1H), 5.18(d, J=13.0 Hz, 1H), 7.10(d, J=7.6 Hz, 2H), 7.37(d, J=7.6 Hz, 2H), 7.61-7.93(m, 5H), 9.24(s, 1H), 15.17 (brs, 1H).
$^{13}$C NMR(100 MHz, DMSO-$d_6$): 20.7, 25.1, 36.9, 48.5, 71.1, 90.4, 110.4, 118.7, 119.6, 121.9, 123.1, 124.6, 125.6, 129.0, 131.9, 135.0, 136.3, 139.8, 140.7, 149.2.

EXAMPLE 28

Preparation of 1-{2-(imidazole-1-yl)ethyl}-1-(4-tolyl)-1,3-dihydro-5-isobenzofurancarbonitrile $^1$H NMR(400 MHz, CDCl$_3$): 2.31(s, 3H), 2.57(m, 1H), 2.74(m, 1H), 3.96(m, 2H), 5.16(d, J=13.2 Hz, 1H), 5.21(d, J=13.2 Hz, 1H), 6.82(s, 1H), 7.02(s, 1H), 7.15(d, J=8.0 Hz, 2H), 7.33(d, J=8.0 Hz, 2H), 7.44(d, J=8.0 Hz, 1H), 7.49(s, 1H), 7.58(d, J=8.0 Hz, 1H), 7.69(s, 1H).

EXAMPLE 29

Preparation of 1-{2-(imidazole-1-yl)ethyl}-1-(4-tolyl)-1,3-dihydro-5-isobenzofurancarbonitrile hydrochloride $^1$H NMR(400 MHz, DMSO-$d_6$): 2.23(s, 3H), 2.80(m, 1H), 2.95(m, 1H), 4.11(m, 2H), 5.15(d, J=13.4 Hz, 1H), 5.25(d, J=13.4 Hz, 1H), 7.13(d, J=7.2 Hz, 2H), 7.44(d, J=7.2 Hz, 2H), 7.57(s, 1H), 7.70-7.77(m, 3H), 7.78(s, 1H), 90.8(s, 1H), 14.89(brs, 1H).
$^{13}$C NMR(100 MHz, DMSO-$d_6$): 20.6, 40.1, 44.7, 71.2, 89.2, 110.4, 118.6, 119.2, 121.8, 122.9, 124.3, 125.5, 128.9, 131.8, 134.9, 136.5, 139.4, 140.2, 148.1.

EXAMPLE 30

Preparation of 1-{3-(pyrazole-1-yl)propyl}-1-(4-tolyl)-1,3-dihydro-5-isobenzofurancarbonitrile $^1$H NMR(400 MHz, CDCl$_3$): 1.79(m, 1H), 1.88(m, 1H), 2.05(m, 1H), 2.20(m, 1H), 2.28(s, 3H), 4.20(t, J=6.8 Hz, 2H), 5.14(m, 2H), 6.26(s, 1H), 7.11(d, J=8.0 Hz, 2H), 7.23-7.35 (m, 4H), 7.45(s, 1H), 7.52-7.56(m, 2H).

EXAMPLE 31

Preparation of 1-{3-(pyrazole-1-yl)propyl}-1-(4-tolyl)-1,3-dihydro-5-isobenzofurancarbonitrile hydrochloride $^1$H NMR(400 MHz, DMSO-$d_6$): 1.57(m, 1H), 1.66(m, 1H), 2.09(m, 2H), 2.18(s, 3H), 4.13(m, 2H), 5.06(d, J=13.2 Hz, 1H), 5.13(d, J=13.2 Hz, 1H), 6.29(s, 1H), 7.07(d J=7.4 Hz, 2H), 7.33(d, J=7.4 Hz, 2H), 7.58-7.70(m, 4H), 7.79(s, 1H), 13.47(brs, 1H).
$^{13}$C NMR(100 MHz, DMSO-$d_6$): 20.6, 25.2, 37.1, 50.9, 70.9, 90.4, 105.3, 110.2, 118.7, 122.9, 124.5, 125.4, 128.8, 130.8, 131.8, 136.1, 137.3, 139.7, 140.7, 149.2.

EXAMPLE 32

Preparation of 1-{2-(pyrazole-1-yl)ethyl}-1-(4-tolyl)-1,3-dihydro-5-isobenzofurancarbonitrile $^1$H NMR(400 MHz, CDCl$_3$): 2.29(s, 3H), 2.79(m, 2H), 4.15(m, 2H), 5.19(m, 2H), 6.11(s, 1H), 7.13(d, J=8.4 Hz, 2H), 7.17(s, 1H), 7.34(d, J=8.4 Hz, 2H), 7.39(d, J=7.6 Hz, 1H), 7.45-7.53(m, 3H).

EXAMPLE 33

Preparation of 1-{2-(pyrazole-1-yl)ethyl}-1-(4-tolyl)-1,3-dihydro-5-isobenzofurancarbonitrile hydrochloride $^1$H NMR(400 MHz, DMSO-$d_6$): 2.21(s, 3H), 2.77(m, 2H), 4.05(m, 2H), 5.13(d, J=12.8 Hz, 1H), 5.24(d, J=12.8 Hz, 1H), 6.18(s, 1H), 7.12(d, J=7.0 Hz, 2H), 7.43(d, J=7.0 Hz, 2H), 7.51(s, 1H), 7.60-7.80(m, 4H), 11.81(brs, 1H).
$^{13}$C NMR(100 MHz, DMSO-$d_6$): 20.6, 40.2, 47.1, 71.2, 89.3, 105.2, 110.3, 118.6, 122.9, 124.4, 125.4, 128.9, 130.6, 131.8, 136.3, 137.4, 139.1, 140.4, 148.4.

EXAMPLE 34

Preparation of 1-(4-dimethylaminophenyl)-1-{3-(dimethylamino)propyl}-1,3-dihydro-5-isobenzofurancarbonitrile $^1$H NMR(400 MHz, CDCl$_3$): 1.32(m, 1H), 1.50(m, 1H), 2.08-2.27(m, 10H), 2.91(s, 6H), 5.29(m, 2H), 6.66(d, J=7.2 Hz, 2H), 7.27(d, J=7.2 Hz, 2H), 7.35(d, J=8.0 Hz, 1H), 7.47(s, 1H), 7.55(d, J=8.0 Hz, 1H).

EXAMPLE 35

Preparation of 1-(4-dimethylaminophenyl)-1-{3-(dimethylamino)propyl}-1,3-dihydro-5-isobenzofurancarbonitrile oxalate $^1$H NMR(400 MHz, DMSO-$d_6$): 1.41(m, 1H), 1.53(m, 1H), 2.14(m, 2H), 2.62(s, 6H), 2.83(s, 6H), 2.97(t, J=8.0 Hz, 2H), 5.08(d, J=13.6 Hz, 1H), 5.17(d, J=13.6 Hz, 1H), 6.65(d, J=8.0 Hz, 2H), 7.28(d, J=8.0 Hz, 2H), 7.62(d, J=7.6 Hz, 1H), 7.75(d, J=7.6 Hz, 1H), 7.77(s, 1H).
$^{13}$C NMR (100 MHz, DMSO-$d_6$): 19.3, 30.7, 36.8, 42.1, 56.6, 70.8, 90.3, 110.0, 112.0, 118.7, 122.8, 125.3, 125.4, 130.9, 131.7, 139.6, 149.3, 149.7, 164.1.

EXAMPLE 36

Preparation of 1-(4-dimethylaminophenyl)-1-{3-(dimethylamino)propyl}-1,3-dihydro-5-isobenzofurancarbonitrile hydrochloride $^1$H NMR(400 MHz, DMSO-$d_6$): 1.44(m, 1H), 1.52(m, 1H), 2.23(t, J=7.2 Hz, 2H), 2.69(s, 3H), 2.70(s, 3H), 2.94(s, 6H), 3.00(m, 2H), 5.13(d, J=13.4 Hz, 1H), 5.21(d, J=13.4 Hz, 1H), 6.64(d, J=7.8 Hz, 2H), 7.25(d, J=7.8 Hz, 2H), 7.70-7.80 (m, 3H), 9.91(brs, 1H).

¹³C NMR (100 MHz, DMSO-d₆): 19.3, 36.8, 41.8, 41.9, 56.2, 71.2, 90.2, 110.5, 112.0, 118.6, 122.9, 125.6, 126.0, 130.9, 131.9, 139.6, 148.4, 149.3.

EXAMPLE 37

Preparation of 1-(4-dimethylaminophenyl)-1-{3-(imidazole-1-yl)propyl}-1,3-dihydro-5-isobenzofurancarbonitrile ¹H NMR(400 MHz, CDCl₃): 1.69(m, 1H), 1.80(m, 1H), 2.01(m, 1H), 2.17(m, 1H), 2.92(s, 6H), 3.92(m, 2H), 5.30(m, 2H), 6.66(d, J=7.4 Hz, 2H), 6.83(s, 1H), 7.04(s, 1H), 7.19-7.23(m, 3H), 7.41(s, 1H), 7.48(s, 1H), 7.56(d, J=7.6 Hz, 1H).

EXAMPLE 38

Preparation of 1-(4-dimethylaminophenyl)-1-{3-(imidazole-1-yl)propyl}-1,3-dihydro-5-isobenzofurancarbonitrile hydrochloride ¹H NMR(400 MHz, DMSO-d₆): 1.62(m, 1H), 1.72(m, 1H), 2.12(m, 2H), 2.88(s, 6H), 4.15(t, J=7.0 Hz, 2H), 5.09(d, J=13.6 Hz, 1H), 5.15(d, J=13.6 Hz, 1H), 6.82(d, J=8.2 Hz, 2H), 7.34(d, J=8.2 Hz, 2H), 7.62-794(m, 5H), 9.08(s, 1H).

EXAMPLE 39

Preparation of 1-{3-(dimethylamino)propyl}-1-(2-thienyl)-1,3-dihydro-5-isobenzofurancarbonitrile ¹H NMR(400 MHz, CDCl₃): 1.56(m, 1H), 1.73(m, 1H), 2.25(m, 1H), 2.35-2.50(m,7H), 2.62(m, 2H), 5.19(d, J=13.2 Hz, 1H), 5.24(d, J=13.2 Hz, 1H), 6.92-6.95(m, 2H), 7.19(m, 1H), 7.41(d, J=7.6 Hz, 1H), 7.50(s, 1H), 7.60(d, J=7.6 Hz, 1H).

EXAMPLE 40

Preparation of 1-{3-(dimethylamino)propyl}-1-(2-thienyl)-1,3-dihydro-5-isobenzofurancarbonitrile oxalate ¹H NMR(400 MHz, DMSO-d₆): 1.41(m, 1H), 1.59(m, 1H), 2.26(t, J=7.6 Hz, 2H), 2.62(s, 6H), 2.97(t, J=7.8 Hz, 2H), 5.16(d, J=13.2 Hz, 1H), 5.21(d, J=13.2 Hz, 1H), 6.99(m, 1H), 7.12(d, J=3.6 Hz, 1H), 7.40(d, J=5.2 Hz, 1H), 7.64(d, J=7.8 Hz, 1H), 7.80(d, J=7.8 Hz, 1H), 7.83(s, 1H).
¹³C NMR(100 MHz, DMSO-d₆): 19.2, 37.5, 42.1, 56.4, 71.4, 89.2, 110.7, 118.6, 122.7, 122.8, 124.9, 125.7, 127.4, 132.0, 139.3, 148.1, 148.7, 164.3.

EXAMPLE 41

Preparation of 1-{3-(dimethylamino)propyl}-1-(2-thienyl)-1,3-dihydro-5-isobenzofurancarbonitrile hydrochloride ¹H NMR(400 MHz, DMSO-d₆): 1.45(m, 1H), 1.56(m, 1H), 2.29(t, J=7.6 Hz, 2H), 2.64(s, 3H), 2.65(s, 3H), 3.01(m, 2H), 5.17(d, J=13.2 Hz, 1H), 5.22(d, J=13.2 Hz, 1H), 7.00(m, 1H), 7.13(d, J=3.6 Hz, 1H), 7.40(d, J=5.2 Hz, 1H), 7.67(d, J=7.6 Hz, 1H), 7.82(d, J=8.2 Hz, 1H), 7.85(s, 1H), 9.92(brs, 1H).
¹³C NMR (100 MHz, DMSO-d₆): 18.9, 37.5, 41.7, 41.8, 56.1, 71.4, 89.2, 110.7, 118.5, 122.7, 122.8, 124.8, 125.7, 127.3, 132.0, 139.2, 148.1, 148.7.

EXAMPLE 42

Preparation of 1-{2-(dimethylamino)ethyl}-1-(2-thienyl)-1,3-dihydro-5-isobenzofurancarbonitrile ¹H NMR(400 MHz, CDCl₃): 2.58-2.70(m, 8H), 2.80(m, 2H), 5.19(d, J=13.0 Hz, 1H), 5.24(d, J=13.0 Hz, 1H), 6.92-7.00(m, 2H), 7.22(m, 1H), 7.47-7.52(m, 2H), 7.63(d, J=8.0 Hz, 1H).

EXAMPLE 43

Preparation of 1-{2-(dimethylamino)ethyl}-1-(2-thienyl)-1,3-dihydro-5-isobenzofurancarbonitrile hydrochloride ¹H NMR(400 MHz, DMSO-d₆): 2.60-2.78(m, 8H), 2.82(m, 2H), 5.18(d, J=13.4 Hz, 1H), 5.23(d, J=13.4 Hz, 1H), 7.02(m, 1H), 7.25(d, J=2.8 Hz, 1H), 7.42(d, J=4.4 Hz, 1H), 7.69(d, J=7.6 Hz, 1H), 7.82-7.85(m, 2H), 11.21(brs, 1H).
¹³C NMR(100 MHz, DMSO-d₆): 34.5, 41.8, 41.9, 52.3, 71.4, 87.8, 111.0, 118.4, 122.8, 123.0, 125.3, 125.8, 127.5, 132.2, 138.9, 147.4, 147.3.

EXAMPLE 44

Preparation of 1-{3-(imidazole-1-yl)propyl}-1-(2-thienyl)-1,3-dihydro-5-isobenzofurancarbonitrile ¹H NMR(400 MHz, CDCl₃): 1.78(m, 1H), 1.92(m, 1H), 2.10(m, 1H), 2.28(m, 1H), 4.07(t, J=7.0 Hz, 2H), 5.18(d, J=12.8 Hz, 1H), 5.25(d, J=12.8 Hz, 1H), 6.86(m, 1H), 6.91(s, 1H), 6.95(m, 1H), 7.14(s, 1H), 7.22(m, 1H), 7.32(d, J=8.2 Hz, 1H), 7.52(s, 1H), 7.61(d, J=8.2 Hz, 1H), 7.95(s, 1H).

EXAMPLE 45

Preparation of 1-{3-(imidazole-1-yl)propyl}-1-(2-thienyl)-1,3-dihydro-5-isobenzofurancarbonitrile oxalate ¹H NMR(400 MHz, DMSO-d₆): 1.55(m, 1H), 1.75(m, 1H), 2.18(m, 2H), 4.05(t, J=7.0 Hz, 2H), 5.16(m, 2H), 6.98(m, 1H), 7.06(d, J=3.2 Hz, 1H), 7.25(s, 1H), 7.38(d, J=4.8 Hz, 1H), 7.41(s, 1H), 7.60(d, J=7.8 Hz, 1H), 7.80(d, J=8.0 Hz, 1H), 7.81(s, 1H), 8.34(s, 1H).
¹³C NMR(100 MHz, DMSO-d₆): 25.3, 37.6, 47.0, 71.4, 89.2, 110.7, 118.5, 120.4, 122.6, 122.7, 123.8, 124.8, 125.7, 127.3, 132.0, 136.0, 139.2, 148.1, 148.7, 162.7.

EXAMPLE 46

Preparation of 1-{3-(imidazole-1-yl)propyl}-1-(2-thienyl)-1,3-dihydro-5-isobenzofurancarbonitrile hydrochloride ¹H NMR(400 MHz, DMSO-d₆): 1.61(m, 1H), 1.79(m, 1H), 2.21(m, 2H), 4.02(t, J=7.0 Hz, 2H), 5.20(m, 2H), 6.98(m, 1H), 7.08(d, J=3.6 Hz, 1H), 7.39(d, J=4.8 Hz, 1H), 7.63(d, J=7.8 Hz, 1H), 7.65(s, 1H), 7.72(s, 1H), 7.81(d, J=7.8 Hz, 1H), 7.83(s, 1H), 9.09(s, 1H), 14.42(brs, 1H).

$^{13}$C NMR(100 MHz, DMSO-d$_6$): 24.8, 37.3, 48.2, 71.4, 89.1, 110.7, 118.5, 119.5, 121.7, 122.7, 122.8, 124.8, 125.7, 127.3, 132.0, 134.9, 139.2, 148.0, 148.6.

EXAMPLE 47

Preparation of 1-{2-(imidazole-1-yl)ethyl}-1-(2-thienyl)-1,3-dihydro-5-isobenzofurancarbonitrile $^1$H NMR(400 MHz, CDCl$_3$): 2.66(m, 1H), 2.84(m, 1H), 4.07(m, 2H), 5.22(d, J=13.2 Hz, 1H), 5.28(d, J=13.2 Hz, 1H), 6.88(s, 1H), 6.96-6.99(m, 2H), 7.07(s, 1H), 7.25(m, 1H), 7.43(d, J=8.0 Hz, 1H), 7.55(s, 1H), 7.63(d, J=8.0 Hz, 1H), 7.90(s, 1H).

EXAMPLE 48

Preparation of 1-{2-(imidazole-1-yl)ethyl}-1-(2-thienyl)-1,3-dihydro-5-isobenzofurancarbonitrile hydrochloride $^1$H NMR(400 MHz, DMSO-d$_6$): 2.95(m, 2H), 4.16(m, 2H), 5.21(m, 2H), 7.00(m, 1H), 7.22(d, J=2.4 Hz, 1H), 7.41 (d, J=4.4 Hz, 1H), 7.57-7.75(m, 5H), 9.12(s, 1H), 14.94(brs, 1H).
$^{13}$C NMR(100 MHz, DMSO-d$_6$): 40.1, 44.5, 71.5, 88.0, 110.8, 118.5, 119.1, 121.8, 122.8, 123.0, 125.1, 125.8, 127.5, 132.0, 134.9, 139.0, 147.2, 148.0.

EXAMPLE 49

Preparation of 1-{3-(pyrazole-1-yl)propyl}-1-(2-thienyl)-1,3-dihydro-5-isobenzofurancarbonitrile $^1$H NMR(400 MHz, CDCl$_3$): 1.82(m, 1H), 1.99(m, 1H), 2.14(m, 1H), 2.29(m, 1H), 4.26(t, J=7.0 Hz, 2H), 5.18(d, J=13.0 Hz, 1H), 5.24(d, J=13.0 Hz, 1H), 6.30(s, 1H), 6.86(s, 1H), 6.93(m, 1H), 7.20(m, 1H), 7.32(d, J=8.0 Hz, 1H), 7.40(s, 1H), 7.51(s, 1H), 7.57-7.61(m, 2H).

EXAMPLE 50

Preparation of 1-{3-(pyrazole-1-yl)propyl}-1-(2-thienyl)-1,3-dihydro-5-isobenzofurancarbonitrile hydrochloride $^1$H NMR(400 MHz, DMSO-d$_6$): 1.56(m, 1H), 1.74(m, 1H), 2.16(m, 2H), 4.14(m, 2H), 5.13(m, 2H), 6.26(s, 1H), 6.94(s, 1H), 7.03(s, 1H), 7.33(s, 1H), 7.53-7.57(m, 2H), 7.73-7.79(m, 2H), 8.27(s, 1H), 13.61(brs, 1H).
$^{13}$C NMR(100 MHz, DMSO-d$_6$): 25.1, 37.8, 50.8, 71.4, 89.3, 105.3, 110.9, 118.6, 122.6, 122.7, 124.8, 125.7, 127.3, 130.7, 132.0, 137.4, 139.3, 148.2, 148.8.

EXAMPLE 51

Preparation of 1-{2-(pyrazole-1-yl)ethyl}-1-(2-thienyl)-1,3-dihydro-5-isobenzofurancarbonitrile $^1$H NMR(400 MHz, CDCl$_3$): 2.87(m, 2H), 4.22(m, 2H), 5.26(m, 2H), 6.13(s, 1H), 6.92-6.96(m, 2H), 7.19-7.22(m, 2H), 7.34(d, J=7.6 Hz, 1H), 7.47(s, 1H), 7.51(s, 1H), 7.55(d, J=7.6 Hz, 1H).

EXAMPLE 52

Preparation of 1-{2-(pyrazole-1-yl)ethyl}-1-(2-thienyl)-1,3-dihydro-5-isobenzofurancarbonitrile hydrochloride $^1$H NMR(400 MHz, DMSO-d$_6$): 2.83(m, 2H), 4.11(m, 2H), 5.20(m, 2H), 6.19(s, 1H), 6.95(s, 1H), 7.15(s, 1H), 7.36 (s, 1H), 7.50-7.59(m, 2H), 7.68-7.76(m, 2H), 8.23(s, 1H), 14.18(brs, 1H).
$^{13}$C NMR(100 MHz, DMSO-d$_6$): 40.5, 46.9, 71.7, 88.1, 105.4, 110.7, 118.6, 122.8, 122.9, 125.0, 125.7, 127.5, 131.1, 132.0, 133.3, 139.0, 147.5, 148.4.

EXAMPLE 53

Preparation of 1-(4-fluorophenyl)-1-{3-(imidazole-1-yl)propyl}-1,3-dihydro-5-isobenzofurancarbonitrile $^1$H NMR(400 MHz, CDCl$_3$): 1.68(m, 1H), 1.76(m, 1H), 1.99(m, 1H), 2.14(m, 1H), 3.96(t, J=6.8 Hz, 2H), 5.12(m, 2H), 6.82(s, 1H), 6.98(m, 2H), 7.05(s, 1H), 7.28-7.38(m, 3H), 7.48(s, 1H), 7.57(d, J=8.0 Hz, 1H), 7.64(s, 1H).

EXAMPLE 54

Preparation of 1-(4-fluorophenyl)-1-{3-(imidazole-1-yl)propyl}-1,3-dihydro-5-isobenzofurancarbonitrile hydrochloride $^1$H NMR(400 MHz, DMSO-d$_6$): 1.62(m, 1H), 1.70(m, 1H), 2.17(m, 2H), 4.15(t, J=7.0 Hz, 2H), 5.13(d, J=13.6 Hz, 1H), 5.19(d, J=13.6 Hz, 1H), 7.15(m, 2H), 7.55(m, 2H), 7.64-7.80(m, 5H), 9.09(s, 1H).
$^{13}$C NMR(100 MHz, DMSO-d$_6$): 24.9, 36.8, 48.3, 71.0, 90.1, 110.4, 115.0(d, $^2J_{CF}$=21 Hz), 118.5, 119.5, 121.7, 123.0, 125.5, 126.7(d, $^3J_{CF}$=8 Hz), 131.9, 134.9, 139.6, 139.7, 148.5, 161.0(d, $^1J_{CF}$=242 Hz).

EXAMPLE 55

Preparation of 1-(4-fluorophenyl)-1-{2-(imidazole-1-yl)ethyl}-1,3-dihydro-5-isobenzofurancarbonitrile $^1$H NMR(400 MHz, CDCl$_3$): 2.79(m, 1H), 2.91(m, 1H), 4.13(m, 2H), 5.15(d, J=13.0 Hz, 1H), 5.23(d, J=13.0 Hz, 1H), 6.93(s, 1H), 7.03(m, 2H), 7.18(s, 1H), 7.48-7.51(m, 3H), 7.61-7.68(m, 2H), 9.03(s, 1H).

EXAMPLE 56

Preparation of 1-(4-fluorophenyl)-1-{2-(imidazole-1-yl)ethyl}-1,3-dihydro-5-isobenzofurancarbonitrile hydrochloride $^1$H NMR(400 MHz, DMSO-d$_6$): 2.81(m, 1H), 2.90(m, 1H), 4.10(m, 2H), 5.17(d, J=13.4 Hz, 1H), 5.25(d, J=13.4 Hz, 1H), 7.18(m, 2H), 7.56-7.62(m, 3H), 7.76-7.78(m, 3H), 7.81 (s, 1H), 8.95(s, 1H), 14.00(brs, 1H).

$^{13}$C NMR(100 MHz, DMSO-d$_6$): 40.1, 44.6, 71.3, 89.0, 110.6, 115.1(d, $^2J_{CF}$=21 Hz), 118.5, 119.2, 121.8, 122.9, 125.6, 126.6(d, 3JCF=8 Hz), 131.9, 135.0, 139.3, 147.6, 162.2(d, $^1J_{CF}$=242 Hz).

EXAMPLE 57

Preparation of 1-(4-fluorophenyl)-1-{3-(pyrazole-1-yl)propyl}-1,3-dihydro-5-isobenzofurancarbonitrile $^1$H NMR(400 MHz, CDCl$_3$): 1.74(m, 1H), 1.90(m, 1H), 2.04(m, 1H), 2.15(m, 1H), 4.09(m, 2H), 5.10(d, J=13.0 Hz, 1H), 5.16(d, J=13.0 Hz, 1H), 6.20(s, 1H), 6.39(s, 1H), 6.97(m, 2H), 7.23-7.35(m, 4H), 7.46(s, 1H), 7.55(d, J=7.6 Hz, 1H).

EXAMPLE 58

Preparation of 1-(4-fluorophenyl)-1-{3-(pyrazole-1-yl)propyl}-1,3-dihydro-5-isobenzofurancarbonitrile hydrochloride $^1$H NMR(400 MHz, DMSO-d$_6$): 1.55(m, 1H), 1.62(m, 1H), 2.12(t, J=7.6 Hz, 2H), 4.05(t, J=7.2 Hz, 2H), 5.10(d, J=13.4 Hz, 1H), 5.16(d, J=13.4 Hz, 1H), 6.17(m, 1H), 6.38(m, 1H), 7.14(m, 2H), 7.37(m, 1H), 7.52(m, 2H), 7.63-7.78(m, 3H).

EXAMPLE 59

Preparation of 1-(4-fluorophenyl)-1-{2-(pyrazole-1-yl)ethyl}-1,3-dihydro-5-isobenzofurancarbonitrile $^1$H NMR(400 MHz, CDCl$_3$): 2.76(m, 2H), 4.12(m, 2H), 5.16(d, J=12.8 Hz, 1H), 5.23(d, J=12.8 Hz, 1H), 6.08(s, 1H), 7.00(m, 2H), 7.14(s, 1H), 7.35(d, J=7.6 Hz, 1H), 7.40-7.44(m, 3H), 7.48(s, 1H), 7.53(d, J=7.6 Hz, 1H).

EXAMPLE 60

Preparation of 1-(4-fluorophenyl)-1-{2-(pyrazole-1-yl)ethyl}-1,3-dihydro-5-isobenzofurancarbonitrile hydrochloride $^1$H NMR(400 MHz, DMSO-d$_6$): 2.77(m, 2H), 4.02(d, J=7.0 Hz, 2H), 5.17(d, J=13.4 Hz, 1H), 5.25(d, J=13.4 Hz, 1H), 6.15(s, 1H), 7.14(m, 2H), 7.43(s, 1H), 7.59-7.65(m, 3H), 7.73-7.77(m, 3H), 12.03(brs, 1H).

$^{13}$C NMR(100 MHz, DMSO-d$_6$): 40.4, 47.0, 71.3, 89.1, 105.0, 110.5, 115.1 (d, $^2J_{CF}$=20 Hz), 118.6, 123.0, 125.5, 126.7 (d, $^3J_{CF}$=8 Hz), 130.1, 131.9, 137.8, 139.4, 139.6 (d, $^4J_{CF}$=3 Hz), 148.1, 161.1 (d, $^1J_{CF}$=242 Hz).

EXAMPLE 61

Preparation of 1-(4-chlorophenyl)-1-{3-(imidazole-1-yl)propyl}-1,3-dihydro-5-isobenzofurancarbonitrile $^1$H NMR(400 MHz, CDCl$_3$): 1.72(m, 2H), 2.00(m, 1H), 2.11(m, 1H), 3.97(t, J=7.0 Hz, 2H), 5.14(m, 2H), 6.83(s, 1H), 7.06(s, 1H), 7.24-7.32(m, 5H), 7.48(s, 1H), 7.57(d, J=8.0 Hz, 1H), 7.66(s, 1H).

EXAMPLE 62

Preparation of 1-(4-chlorophenyl)-1-{3-(imidazole-1-yl)propyl}-1,3-dihydro-5-isobenzofurancarbonitrile hydrochloride $^1$H NMR(400 MHz, DMSO-d$_6$): 1.62(m, 2H), 2.16(m, 2H), 4.14(t, J=7.0 Hz, 2H), 5.13(d, J=13.6 Hz, 1H), 5.19(d, J=13.6 Hz, 1H), 7.39(d, J=8.6 Hz, 2H), 7.54(d, J=8.6 Hz, 2H), 7.64(s, 1H), 7.71-7.80(m, 4H), 9.08(s, 1H).

$^{13}$C NMR(100 MHz, DMSO-d$_6$): 24.8, 36.6, 48.3, 71.1, 90.0, 110.5, 118.5, 119.5, 121.7, 123.0, 125.6, 126.6, 128.2, 131.8, 131.9, 134.9, 139.6, 142.5, 148.3.

EXAMPLE 63

Preparation of 1-(4-chlorophenyl)-1-{2-(imidazole-1-yl)ethyl}-1,3-dihydro-5-isobenzofurancarbonitrile $^1$H NMR(400 MHz, CDCl$_3$): 2.60(m, 1H), 2.71(m, 1H), 3.96(m, 2H), 5.15(d, J=13.0 Hz, 1H), 5.22(d, J=13.0 Hz, 1H), 6.81(s, 1H), 7.01(s, 1H), 7.30-7.41(m, 4H), 7.45(d, J=8.4 Hz, 1H), 7.51(s, 1H), 7.60(d, J=8.4 Hz, 1H), 7.74(s, 1H).

EXAMPLE 64

Preparation of 1-(4-chlorophenyl)-1-{2-(imidazole-1-yl)ethyl}-1,3-dihydro-5-isobenzofurancarbonitrile hydrochloride $^1$H NMR(400 MHz, DMSO-d$_6$): 2.81(m, 1H), 2.91(m, 1H), 4.12(m, 2H), 5.17(d, J=13.4 Hz, 1H), 5.25(d, J=13.4 Hz, 1H), 7.42(d, J=7.2 Hz, 2H), 7.57-7.61(m, 3H), 7.68-7.78(m, 3H), 7.82(s, 1H), 8.97(s, 1H), 14.00(brs, 1H).

$^{13}$C NMR(100 MHz, DMSO-d$_6$): 40.1, 44.6, 71.4, 89.0, 110.7, 118.5, 119.2, 121.8, 122.9, 125.6, 126.5, 128.3, 131.9, 132.1, 135.0, 139.3, 142.1, 147.3.

EXAMPLE 65

Preparation of 1-(4-chlorophenyl)-1-{3-(pyrazole-1-yl)propyl}-1,3-dihydro-5-isobenzofurancarbonitrile $^1$H NMR(400 MHz, CDCl$_3$): 1.74(m, 1H), 1.83(m, 1H), 2.03(m, 1H), 2.15(m, 1H), 4.10(m, 2H), 5.10(d, J=13.0 Hz, 1H), 5.15(d, J=13.0 Hz, 1H), 6.20(s, 1H), 7.24-7.32(m, 5H), 7.45-7.46(m, 2H), 7.55(d, J=8.0 Hz, 1H), 7.73(s, 1H).

EXAMPLE 66

Preparation of 1-(4-chlorophenyl)-1-{3-(pyrazole-1-yl)propyl}-1,3-dihydro-5-isobenzofurancarbonitrile hydrochloride $^1$H NMR(400 MHz, DMSO-d$_6$): 1.59(m, 2H), 2.12(m, 2H), 4.05(d, J=7.2 Hz, 2H), 5.11(d, J=13.4 Hz, 1H), 5.17(d, J=13.4 Hz, 1H), 6.17(m, 1H), 7.35-7.38(m, 3H), 7.52(d, J=8.4 Hz, 2H), 7.63-7.69(m, 2H), 7.76-7.78(m, 2H).

$^{13}$C NMR(100 MHz, DMSO-d$_6$): 25.2, 37.1, 50.8, 71.1, 90.2, 105.0, 110.5, 118.6, 122.9, 125.6, 126.6, 128.2, 130.1, 131.9, 133.3, 137.8, 139.6, 142.7, 148.5.

EXAMPLE 67

Preparation of 1-(4-chlorophenyl)-1-{2-(pyrazole-1-yl)ethyl}-1,3-dihydro-5-isobenzofurancarbonitrile $^1$H NMR(400 MHz, CDCl$_3$): 2.78(m, 2H), 4.14(t, J=7.6 Hz, 2H), 5.16(d, J=13.2 Hz, 1H), 5.23(d, J=13.2 Hz, 1H), 6.09(s, 1H), 7.14(s, 1H), 7.27-7.43(m, 5H), 7.44(s, 1H), 7.47 (s, 1H), 7.53(s, 1H).

EXAMPLE 68

Preparation of 1-(4-chlorophenyl)-1-{2-(pyrazole-1-yl)ethyl}-1,3-dihydro-5-isobenzofurancarbonitrile hydrochloride $^1$H NMR(400 MHz, DMSO-d$_6$): 2.75(m, 2H), 3.98(m, 2H), 5.18(d, J=14.0 Hz, 1H), 5.28(d, J=14.0 Hz, 1H), 6.10(m, 1H), 7.33-7.41(m, 3H), 7.58-7.63(m, 3H), 7.52-7.79(m, 3H).
$^{13}$C NMR(100 MHz, DMSO-d$_6$): 40.3, 46.9, 71.4, 89.1, 104.9, 110.6, 118.6, 122.9, 125.5, 126.5, 128.3, 129.9, 131.9, 137.9, 139.4, 142.4, 143.8, 147.8.

The structures of the examples 1 to 68 are described in Tables 1 and 2, below.

TABLE 1

| Example | R$^1$ | n | R$^2$ | salt |
|---|---|---|---|---|
| 1 | 4-methoxyphenyl | 3 | dimethylamino | |
| 2 | " | 3 | " | Oxalic acid salt |
| 3 | " | 3 | " | HCl salt |
| 4 | " | 3 | 1-imidazolyl | |
| 5 | " | 3 | " | HCl salt |
| 6 | " | 2 | " | |
| 7 | " | 2 | " | HCl salt |
| 8 | " | 3 | 1-pyrazolyl | |
| 9 | " | 3 | " | HCl salt |
| 10 | " | 2 | " | |
| 11 | " | 2 | " | HCl salt |
| 12 | phenyl | 3 | dimethylamino | |
| 13 | " | 3 | " | HCl salt |
| 14 | " | 2 | " | |
| 15 | " | 2 | " | HCl salt |
| 16 | " | 3 | 1-imidazolyl | |
| 17 | " | 3 | " | HCl salt |
| 18 | " | 2 | " | |
| 19 | " | 2 | " | HCl salt |
| 20 | " | 2 | 1-pyrazolyl | |
| 21 | " | 2 | " | HCl salt |
| 22 | 4-tolyl | 3 | dimethylamino | |
| 23 | " | 3 | " | HCl salt |
| 24 | " | 2 | " | |
| 25 | " | 2 | " | HCl salt |
| 26 | " | 3 | 1-imidazolyl | |
| 27 | " | 3 | " | HCl salt |
| 28 | " | 2 | " | |
| 29 | " | 2 | " | HCl salt |
| 30 | " | 3 | 1-pyrazolyl | |
| 31 | " | 3 | " | HCl salt |
| 32 | " | 2 | " | |
| 33 | " | 2 | " | HCl salt |

TABLE 2

| Example | R$^1$ | n | R$^2$ | salt |
|---|---|---|---|---|
| 34 | 4-dimethylaminophenyl | 3 | dimethylamino | |
| 35 | " | 3 | " | Oxalic acid salt |
| 36 | " | 3 | " | HCl salt |
| 37 | " | 3 | 1-imidazolyl | |
| 38 | " | 3 | " | HCl salt |
| 39 | 2-thienyl | 3 | dimethylamino | |
| 40 | " | 3 | " | Oxalic acid salt |
| 41 | " | 3 | " | HCl salt |
| 42 | " | 2 | " | |
| 43 | " | 2 | " | HCl salt |
| 44 | " | 3 | 1-imidazolyl | |
| 45 | " | 3 | " | Oxalic acid salt |
| 46 | " | 3 | " | HCl salt |
| 47 | " | 2 | " | |
| 48 | " | 2 | " | HCl salt |
| 49 | " | 3 | 1-pyrazolyl | |
| 50 | " | 3 | " | HCl salt |
| 51 | " | 2 | " | |
| 52 | " | 2 | " | HCl salt |
| 53 | 4-fluorophenyl | 3 | 1-imidazolyl | |
| 54 | " | 3 | " | HCl salt |
| 55 | " | 2 | " | |
| 56 | " | 2 | " | HCl salt |
| 57 | " | 3 | 1-pyrazolyl | |
| 58 | " | 3 | " | HCl salt |
| 59 | " | 2 | " | |
| 60 | " | 2 | " | HCl salt |
| 61 | 4-chlorophenyl | 3 | 1-imidazolyl | |
| 62 | " | 3 | " | HCl salt |
| 63 | " | 2 | " | |
| 64 | " | 2 | " | HCl salt |
| 65 | " | 3 | 1-pyrazolyl | |
| 66 | " | 3 | " | HCl salt |
| 67 | " | 2 | " | |
| 68 | " | 2 | " | HCl salt |

TEST EXAMPLE 1

Evaluation of Ejaculation-delaying Effect

The compounds prepared in the above examples were evaluated to determine whether they have an effect of delaying ejaculation. The evaluation was carried out using an animal model according to a method described in Yonezawa et al., Life Sci. 2000, 67(25) p 3031-9. Male Wistar rats weighing 240-260 g were used. Each compound was suspended in 1% HPMC, and then administered orally to each animal. After 60 min, the animals were anesthetized and fixed. 20 min later, para-chloroamphetamine (p-PCA) was intraperitoneally administered in a dose of 5 mg/kg in order to induce ejaculation. Then, the ejaculatory response to p-PCA was observed in anesthetized rats over 30 min. An ejaculatory response was considered to be elicited when rhythmic contraction of bulbocavernosus muscles and semen discharge occurs. Six or more animals were used for each compound. A Fisher's extract test was performed for the comparison of the proportion of responding rats (ejaculated rats) to determine significance of difference between a treatment group and a vehicle control. The time to reach ejaculation was expressed as mean±standard deviation.

The compounds prepared in Examples 1 to 68 were found to have good inhibitory effects on ejaculation. The ejaculation-inhibiting effects of representative compounds are given in Table 3, below. Each test compound was administered at a dose of 50 mg/kg. Ejaculation was elicited in all seven animals of a control group. In contrast, the administration of the compounds prepared in Examples 1 to 68 significantly reduced the number of responding rats. These results indicated that the present compounds are very effective in inhibiting ejaculation. Citalopram, which is conventional SSRI drug known to have ejaculation-delaying effects, was used as control compound.

TABLE 3

| Compound | Ratio | Latency |
|---|---|---|
| Control | 7/7 | 778 ± 344 |
| Ex. 1 | 5/9 | 1024 ± 256 |
| Ex. 2 | 0/9 | ND |
| Ex. 3 | 1/6 | 1234 |
| Ex. 4 | 4/9 | 1300 ± 124 |
| Ex. 5 | 3/7 | 986 ± 342 |
| Ex. 6 | 4/7 | 889 ± 284 |
| Ex. 7 | 5/9 | 963 ± 304 |
| Ex. 8 | 4/9 | 1230 ± 421 |
| Ex. 9 | 4/7 | 950 ± 245 |
| Ex. 10 | 4/9 | 889 ± 360 |
| Ex. 11 | 3/7 | 974 ± 289 |
| Ex. 12 | 4/9 | 1025 ± 189 |
| Ex. 13 | 1/6 | 327 |
| Ex. 14 | 3/7 | 1032 ± 451 |
| Ex. 15 | 4/9 | 1345 ± 510 |
| Ex. 16 | 4/9 | 856 ± 365 |
| Ex. 17 | 3/6 | 949 ± 330 |
| Ex. 18 | 3/7 | 691 ± 361 |
| Ex. 19 | 5/9 | 954 ± 275 |
| Ex. 20 | 3/7 | 978 ± 378 |
| Ex. 21 | 4/7 | 799 ± 387 |
| Ex. 22 | 3/7 | 830 ± 287 |
| Ex. 23 | 4/7 | 967 ± 274 |
| Ex. 24 | 3/7 | 1021 ± 367 |
| Ex. 25 | 4/9 | 841 ± 254 |
| Ex. 26 | 4/7 | 904 ± 304 |
| Ex. 27 | 3/7 | 864 ± 257 |
| Ex. 28 | 3/7 | 734 ± 451 |
| Ex. 29 | 5/9 | 1054 ± 287 |
| Ex. 30 | 3/7 | 876 ± 300 |
| Ex. 31 | 3/9 | 754 ± 401 |
| Ex. 32 | 4/9 | 1000 ± 401 |
| Ex. 33 | 3/7 | 698 ± 374 |
| Ex. 34 | 4/9 | 807 ± 304 |
| Ex. 35 | 0/9 | ND |
| Ex. 36 | 2/6 | 554 ± 77 |
| Ex. 37 | 4/7 | 950 ± 241 |
| Ex. 38 | 4/7 | 764 ± 304 |
| Ex. 39 | 5/9 | 854 ± 287 |
| Ex. 40 | 3/9 | 876 ± 110 |
| Ex. 41 | 1/7 | 702 |
| Ex. 42 | 4/9 | 906 ± 275 |
| Ex. 43 | 3/7 | 888 ± 275 |
| Ex. 44 | 4/7 | 904 ± 350 |
| Ex. 45 | 2/9 | 676 ± 10 |
| Ex. 46 | 0/7 | ND |
| Ex. 47 | 4/7 | 814 ± 278 |
| Ex. 48 | 3/7 | 904 ± 321 |
| Ex. 49 | 5/9 | 807 ± 301 |
| Ex. 50 | 3/7 | 979 ± 347 |
| Ex. 51 | 4/7 | 1042 ± 451 |
| Ex. 52 | 3/7 | 869 ± 274 |
| Ex. 53 | 4/9 | 1054 ± 320 |
| Ex. 54 | 5/9 | 1247 ± 352 |
| Ex. 55 | 4/7 | 1450 ± 671 |
| Ex. 56 | 2/6 | 606 ± 130 |
| Ex. 57 | 4/9 | 951 ± 342 |
| Ex. 58 | 4/9 | 850 ± 362 |
| Ex. 59 | 3/7 | 954 ± 287 |
| Ex. 60 | 4/9 | 1010 ± 400 |
| Ex. 61 | 3/7 | 930 ± 247 |
| Ex. 62 | 4/7 | 888 ± 284 |
| Ex. 63 | 3/7 | 904 ± 307 |
| Ex. 64 | 4/7 | 1032 ± 299 |
| Ex. 65 | 5/9 | 801 ± 401 |
| Ex. 66 | 4/7 | 960 ± 350 |
| Ex. 67 | 3/7 | 853 ± 352 |
| Ex. 68 | 4/9 | 908 ± 274 |

Ratio: Number fo responding animals/total animal number
Latency: Time (sec) to display the ejaculatory response
ND: not determined

TEST EXAMPLE 2

Determination of Half-lives of the Compounds in Rats

The half-lives of present compounds were determined as follows. Each compound was administered orally to male Sprague-Dawley rats weighing approximately 270 g at a dose of 10 mg/kg. 5 mg/kg of each compound was suspended in 0.5% methyl-cellulose and then administered to rats. Blood samples were collected 0.017, 0.083, 0.25, 0.5, 1, 2, 3, 5, 7 and 24 hours after administration, and centrifuged at 1,000 rpm for 3 min to separate plasma. The concentration of each compound in plasma was determined using high performance liquid chromatography, which was performed with a mobile phase of 10 mM ammonium formate (pH 3.0) and acetonitrile (50:50), an atlanis dC18 column (21×100 mm, 3 μm) and a flow rate of 0.2 ml/min.

The results are given in Table 4, below. The present compounds displayed Tmax (time to reach maximal plasma concentration) values similar to that of citalopram, which is conventional SSRI drug known to have ejaculation-delaying effects, but showed half-lives three times shorter than that of citalopram. These results indicated that the present compounds are rapidly absorbed into the body and quickly excreted outside the body and thus have a lower risk of incidence of side effects and improved safety.

TABLE 4

| | Citalopram | Ex. 2 | Ex. 35 | Ex. 40 | Ex. 45 |
|---|---|---|---|---|---|
| $T_{1/2}$ (hr) | 3.24 | 1.28 | 3.51 | 1.26 | 1.06 |
| $T_{max}$ (hr) | 0.33 | 0.33 | 0.25 | 0.25 | 0.25 |

TEST EXAMPLE 3

Evaluation of Mechanism of the Present Compounds

The mechanism of the present derivatives was investigated by assessing their inhibitory effects on neurotransmitters and ligand binding affinity to serotonin receptors.

First, the effects of the present compounds on cellular uptake of dopamine, norepinephrine and serotonin were evaluated with human-derived CHO-1, MDCK and HEK-293 cell lines. Each cell line was dosed with $10^{-5}$ μM to $10^4$ μM of the compounds of Examples 2, 35, 40 and 45, and then incubated with [$^3$H]dopamine, [$^3$H]norepinephrine and [$^3$H]serotonin in buffer. After 10 min, the amount of each neurotransmitter taken up into cells was determined by counting radioactivity using a liquid scintillation counter (LSC).

The results are given in Table 5, below. The present compound was found to be not involved in dopamine or norepinephrine reuptake, but was found to act selectively for serotonin to inhibit its reuptake.

In addition, ligand binding to 5HT1A, 5-HT1B and 5-HT2C receptors and 5-HT transporter was evaluated with human-derived recombinant CHO cells, Wistar rat-derived cerebral cortical cells, human-derived recombinant CHO-K1 cells, and human-derived recombinant HEK-293 cells. Each cell line was dosed with $10^{-5}$ μM to $10^4$ μM of the compounds of Examples 2, 35, 40 and 45, and then incubated with a radio-labeled ligand for competitive binding. Ligands used were [41]8-OH-DPAT, [$^{125}$I]Cyanopindolol, [$^3$H]Mesulergine and [$^3$H]Paroxetine, respectively. The competitive binding assay was carried out in 50 mM Tris-HCl buffer at 25° C. or 37° C., for 60 to 90 min.

The radioligand assay revealed that the present compound is highly associated with 5-HT2C receptor and 5-HT transporter. These results indicate that the 1,3-dihydro-5-isobenzofurancarbonitrile derivatives inhibit the ejaculatory response by selectively inhibiting the serotonin reuptake via a serotonin reuptake transporter present in a presynaptic neuron, one among several mechanisms of the central nervous system involved in ejaculation.

TABLE 5

| Test | Receptors | IC50 (micromole) | | | |
|---|---|---|---|---|---|
| | | Ex. 2 | Ex. 35 | Ex. 40 | Ex. 45 |
| Radioligand assay | 5-HT1A | 805 | 1120 | 967 | 898 |
| | 5-HT1B | >1000 | >1000 | >1000 | >1000 |
| | 5-HT2C | 7.12 | 898 | 10.12 | 8.88 |
| | 5-HT transporter | $<0.1 \times 10^{-3}$ | $1 \times 10^{-3}$ | $12.5 \times 10^{-3}$ | $8.7 \times 10^{-3}$ |
| Cellular reuptake assay | Dopamine | 85.7 | 100.2 | 123.5 | 94.2 |
| | Norepinephrine | 36.5 | 53.2 | 69.1 | 67.3 |
| | Serotonin | 0.304 | 0.425 | 0.531 | 0.465 |

TEST EXAMPLE 4

Acute Toxicity Test

To evaluate the safety of the present derivatives in comparison with control drug, an acute toxicity test was conducted with 5-week-old Sprague-Dawley (SD) rats. The present derivatives and citalopram were individually administered orally and intra-venously to SD rats at a single dose. Then, the rats were observed for mortality. The results are given in Table 6, below.

TABLE 6

| | Citalopram | | Ex. 2 | | Ex. 35 | | Ex. 40 | | Ex. 45 | |
|---|---|---|---|---|---|---|---|---|---|---|
| | female | male | female | male | female | male | female | male | female | male |
| Intravenously | 30 | 30 | 70 | 70 | 50 | 50 | 50 | 50 | 50 | 50 |
| Orally | 650 | 650 | 1000 | 1000 | 1000 | 1000 | 800 | 800 | 1000 | 1000 |

As being shown in Table 6, the minimum lethal doses of the compounds of examples 2, 35, 40 and 45 were higher than that of citalopram. It means the compounds of examples 2, 35, 40 and 45 are safer than citalopram. Specially, it was found that the compound of example 2 was over twice safer than citalopram.

TEST EXAMPLE 5

Cardiotoxicity Test

To evaluate the safety of the present derivatives in comparison with control drug, conducted was hERG (human Ether-a-go-go Related Gene) assay which is a representative test of safety medical test. This test was requested to trial institute MDS Pharma., which conducted this test. The results are given in Table 7, below.

TABLE 7

| Compounds | Results (IC50, μM) |
|---|---|
| Citalopram | 4.9 |
| Ex. 2 | 19.4 |
| Ex. 35 | 12.2 |

TABLE 7-continued

| Compounds | Results (IC50, μM) |
|---|---|
| Ex. 40 | 8.7 |
| Ex. 45 | 10.6 |

As shown in Table 7, $IC_{50}$ value of example 3 is about four times higher than that of citalopram. It means the potassium channel inhibition activities of the present derivatives are very low, so the possibility causing cardiotoxicity such as arrhythmia is very small. Therefore, the present derivatives are much safer than citalopram.

TEST EXAMPLE 6

Mutagenicity Test

To evaluate the safety of the present derivatives, mutagenicity test was conducted. Ames test and chromosome aberration test were conducted with the examples 2, 35, 40 and 45. The results are given in Table 8, below.

TABLE 8

| Tests | Tester strains | Concentrations | Results |
|---|---|---|---|
| ames test | Five strains (*Salmonella typhimurium* TA98, | 8, 40, 200, 1000, 2500, 5000 μg/plate (in the | negative |

TABLE 8-continued

| Tests | Tester strains | Concentrations | Results |
|---|---|---|---|
| | 100, 1535, 1537, E. coli WP2 uvrA) | presence/absence of a metabolic activation system) | |
| chromosome aberration test | CHL (Chinese Hamster Lung) cell | 75, 150, 300 μg/ml (in the presence of a metabolic activation system)20, 40, 80 μg/ml (in the absence of a metabolic activation system) | negative |

As shown in Table 8, the results of the examples 2, 35, 40 and 45 were negative. On the other hand, it was reported the result of citalopram was positive in the same test, so it was found the present derivatives are safer than citalopram.

The invention claimed is:

1. A compound represented by Formula 1 or a pharmaceutically acceptable salt thereof:

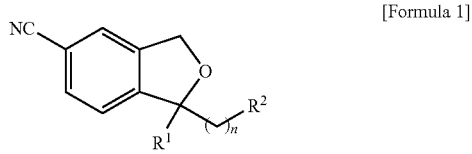

[Formula 1]

wherein, $R^1$ is a phenyl, a phenyl substituted with $C_1$-$C_6$ alkoxy, a phenyl substituted with $C_1$-$C_6$ alkyl, a phenyl substituted with $C_1$-$C_6$ dialkylamino, a phenyl substituted with halogen or a thienyl;

$R^2$ is selected from the group consisting of $C_1$-$C_6$ dialkylamino, pyrazolyl, and imidazolyl, provided that $R^2$ is not $C_1$-$C_6$ dialkylamino when $R^1$ is a phenyl substituted with halogen; and n is an integer from 1 to 3.

2. The compound represented by Formula 1 or the pharmaceutically acceptable salt thereof according to claim 1, wherein, the $R^1$ is a phenyl.

3. The compound represented by Formula 1 or the pharmaceutically acceptable salt thereof according to claim 1, wherein, the $R^1$ is a phenyl substituted with $C_1$-$C_6$ alkoxy.

4. The compound represented by Formula 1 or the pharmaceutically acceptable salt thereof according to claim 3, wherein, the $R^1$ is methoxyphenyl.

5. The compound represented by Formula 1 or the pharmaceutically acceptable salt thereof according to claim 4, wherein,
the $R^2$ is dimethylamino, pyrazolyl, or imidazolyl.

6. The compound represented by Formula 1 or the pharmaceutically acceptable salt thereof according to claim 1, wherein, the $R^1$ is a phenyl substituted with $C_1$-$C_6$ alkyl.

7. The compound represented by Formula 1 or the pharmaceutically acceptable salt thereof according to claim 6, wherein, the $R^1$ is tolyl.

8. The compound represented by Formula 1 or the pharmaceutically acceptable salt thereof according to claim 1, wherein, the $R^1$ is a phenyl substituted with $C_1$-$C_6$ dialkylamino.

9. The compound represented by Formula 1 or the pharmaceutically acceptable salt thereof according to claim 8, wherein, the $R^1$ is dimethylaminophenyl.

10. The compound represented by Formula 1 or the pharmaceutically acceptable salt thereof according to claim 9, wherein,
the $R^2$ is dimethylamino, pyrazolyl, or imidazolyl.

11. The compound represented by Formula 1 or the pharmaceutically acceptable salt thereof according to claim 1, wherein, the $R^1$ is thienyl.

12. The compound represented by Formula 1 or the pharmaceutically acceptable salt thereof according to claim 11, wherein,
the $R^2$ is dimethylamino, pyrazolyl, or imidazolyl.

13. The compound represented by Formula 1 or the pharmaceutically acceptable salt thereof according to claim 1, wherein,
the $R^1$ is a phenyl substituted with halogen; and
the $R^2$ is selected from pyrazolyl, and imidazolyl.

14. The pharmaceutically acceptable salt of the compound represented by Formula 1 according to claim 1, wherein the salt is formed with hydrochloric acid or oxalic acid.

15. The compound represented by Formula 1 or the pharmaceutically acceptable salt thereof according to claim 1 selected from the group consisting of:

1-{3-(dimethylamino)propyl}-1-(4-methoxyphenyl)-1,3-dihydro-5-isobenzofurancarbonitrile;
1-{3-(dimethylamino)propyl}-1-(4-methoxyphenyl)-1,3-dihydro-5-isobenzofurancarbonitrile oxalate;
1-{3-(dimethylamino)propyl}-1-(4-methoxyphenyl)-1,3-dihydro-5-isobenzofurancarbonitrile hydrochloride;
1-{3-(imidazole-1-yl)propyl}-1-(4-methoxyphenyl)-1,3-dihydro-5-isobenzofurancarbonitrile;
1-{3-(imidazole-1-yl)propyl}-1-(4-methoxyphenyl)-1,3-dihydro-5-isobenzofurancarbonitrile hydrochloride;
1-{2-(imidazole-1-yl)ethyl}-1-(4-methoxyphenyl)-1,3-dihydro-5-isobenzofurancarbonitrile;
1-{2-(imidazole-1-yl)ethyl}-1-(4-methoxyphenyl)-1,3-dihydro-5-isobenzofurancarbonitrile hydrochloride;
1-(4-methoxyphenyl)-1-{3-(pyrazole-1-yl)propyl}-1,3-dihydro-5-isobenzofurancarbonitrile;
1-(4-methoxyphenyl)-1-{3-(pyrazole-1-yl)propyl}-1,3-dihydro-5-isobenzofurancarbonitrile hydrochloride;
1-(4-methoxyphenyl)-1-{2-(pyrazole-1-yl)ethyl}-1,3-dihydro-5-isobenzofurancarbonitrile;
1-(4-methoxyphenyl)-1-{2-(pyrazole-1-yl)ethyl}-1,3-dihydro-5-isobenzofurancarbonitrile hydrochloride;
1-{3-(dimethylamino)propyl}-1-phenyl-1,3-dihydro-5-isobenzofurancarbonitrile;
1-{3-(dimethylamino)propyl}-1-phenyl-1,3-dihydro-5-isobenzofurancarbonitrile hydrochloride;
1-{2-(dimethylamino)ethyl}-1-phenyl-1,3-dihydro-5-isobenzofurancarbonitrile;
1-{2-(dimethylamino)ethyl}-1-phenyl-1,3-dihydro-5-isobenzofurancarbonitrile hydrochloride;
1-{3-(imidazole-1-yl)propyl}-1-phenyl-1,3-dihydro-5-isobenzofurancarbonitrile;

1-{3-(imidazole-1-yl)propyl}-1-phenyl-1,3-dihydro-5-isobenzofurancarbonitrile hydrochloride;
1-{2-(imidazole-1-yl)ethyl}-1-phenyl-1,3-dihydro-5-isobenzofurancarbonitrile;
1-{2-(imidazole-1-yl)ethyl}-1-phenyl-1,3-dihydro-5-isobenzofurancarbonitrile hydrochloride;
1-phenyl-1-{2-(pyrazole-1-yl)ethyl}-1,3-dihydro-5-isobenzofurancarbonitrile;
1-phenyl-1-{2-(pyrazole-1-yl)ethyl}-1,3-dihydro-5-isobenzofurancarbonitrile hydrochloride;
1-{3-(dimethylamino)propyl}-1-(4-tolyl)-1,3-dihydro-5-isobenzofurancarbonitrile;
1-{3-(dimethylamino)propyl}-1-(4-tolyl)-1,3-dihydro-5-isobenzofurancarbonitrile hydrochloride;
1-{2-(dimethylamino)ethyl}-1-(4-tolyl)-1,3-dihydro-5-isobenzofurancarbonitrile;
1-{2-(dimethylamino)ethyl}-1-(4-tolyl)-1,3-dihydro-5-isobenzofurancarbonitrile hydrochloride;
1-{3-(imidazole-1-yl)propyl}-1-(4-tolyl)-1,3-dihydro-5-isobenzofurancarbonitrile;
1-{3-(imidazole-1-yl)propyl}-1-(4-tolyl)-1,3-dihydro-5-isobenzofurancarbonitrile hydrochloride;
1-{2-(imidazole-1-yl)ethyl}-1-(4-tolyl)-1,3-dihydro-5-isobenzofurancarbonitrile;
1-{2-(imidazole-1-yl)ethyl}-1-(4-tolyl)-1,3-dihydro-5-isobenzofurancarbonitrile hydrochloride;
1-{3-(pyrazole-1-yl)propyl}-1-(4-tolyl)-1,3-dihydro-5-isobenzofurancarbonitrile;
1-{3-(pyrazole-1-yl)propyl}-1-(4-tolyl)-1,3-dihydro-5-isobenzofurancarbonitrile hydrochloride;
1-{2-(pyrazole-1-yl)ethyl}-1-(4-tolyl)-1,3-dihydro-5-isobenzofurancarbonitrile;
1-{2-(pyrazole-1-yl)ethyl}-1-(4-tolyl)-1,3-dihydro-5-isobenzofurancarbonitrile hydrochloride;
1-(4-dimethylaminophenyl)-1-{3-(dimethylamino)propyl}-1,3-dihydro-5-isobenzofurancarbonitrile;
1-(4-dimethylaminophenyl)-1-{3-(dimethylamino)propyl}-1,3-dihydro-5-isobenzofurancarbonitrile oxalate;
1-(4-dimethylaminophenyl)-1-{3-(dimethylamino)propyl}-1,3-dihydro-5-isobenzofurancarbonitrile hydrochloride;
1-(4-dimethylaminophenyl)-1-{3-(imidazole-1-yl)propyl}-1,3-dihydro-5-isobenzofurancarbonitrile;
1-(4-dimethylaminophenyl)-1-{3-(imidazole-1-yl)propyl}-1,3-dihydro-5-isobenzofurancarbonitrile hydrochloride;
1-{3-(dimethylamino)propyl}-1-(2-thienyl)-1,3-dihydro-5-isobenzofurancarbonitrile;
1-{3-(dimethylamino)propyl}-1-(2-thienyl)-1,3-dihydro-5-isobenzofurancarbonitrile oxalate;
1-{3-(dimethylamino)propyl}-1-(2-thienyl)-1,3-dihydro-5-isobenzofurancarbonitrile hydrochloride;
1-{2-(dimethylamino)ethyl}-1-(2-thienyl)-1,3-dihydro-5-isobenzofurancarbonitrile;
1-{2-(dimethylamino)ethyl}-1-(2-thienyl)-1,3-dihydro-5-isobenzofurancarbonitrile hydrochloride;
1-{3-(imidazole-1-yl)propyl}-1-(2-thienyl)-1,3-dihydro-5-isobenzofurancarbonitrile;
1-{3-(imidazole-1-yl)propyl}-1-(2-thienyl)-1,3-dihydro-5-isobenzofurancarbonitrile oxalate;
1-{3-(imidazole-1-yl)propyl}-1-(2-thienyl)-1,3-dihydro-5-isobenzofurancarbonitrile hydrochloride;
1-{2-(imidazole-1-yl)ethyl}-1-(2-thienyl)-1,3-dihydro-5-isobenzofurancarbonitrile;
1-{2-(imidazole-1-yl)ethyl}-1-(2-thienyl)-1,3-dihydro-5-isobenzofurancarbonitrile hydrochloride;
1-{3-(pyrazole-1-yl)propyl}-1-(2-thienyl)-1,3-dihydro-5-isobenzofurancarbonitrile;
1-{3-(pyrazole-1-yl)propyl}-1-(2-thienyl)-1,3-dihydro-5-isobenzofurancarbonitrile hydrochloride;
1-{2-(pyrazole-1-yl)ethyl}-1-(2-thienyl)-1,3-dihydro-5-isobenzofurancarbonitrile;
1-{2-(pyrazole-1-yl)ethyl}-1-(2-thienyl)-1,3-dihydro-5-isobenzofurancarbonitrile hydrochloride;
1-(4-fluorophenyl)-1-{3-(imidazole-1-yl)propyl}-1,3-dihydro-5-isobenzofurancarbonitrile;
1-(4-fluorophenyl)-1-{3-(imidazole-1-yl)propyl}-1,3-dihydro-5-isobenzofurancarbonitrile hydrochloride;
1-(4-fluorophenyl)-1-{2-(imidazole-1-yl)ethyl}-1,3-dihydro-5-isobenzofurancarbonitrile;
1-(4-fluorophenyl)-1-{2-(imidazole-1-yl)ethyl}-1,3-dihydro-5-isobenzofurancarbonitrile hydrochloride;
1-(4-fluorophenyl)-1-{3-(pyrazole-1-yl)propyl}-1,3-dihydro-5-isobenzofurancarbonitrile;
1-(4-fluorophenyl)-1-{3-(pyrazole-1-yl)propyl}-1,3-dihydro-5-isobenzofurancarbonitrile hydrochloride;
1-(4-fluorophenyl)-1-{2-(pyrazole-1-yl)ethyl}-1,3-dihydro-5-isobenzofurancarbonitrile;
1-(4-fluorophenyl)-1-{2-(pyrazole-1-yl)ethyl}-1,3-dihydro-5-isobenzofurancarbonitrile hydrochloride;
1-(4-chlorophenyl)-1-{3-(imidazole-1-yl)propyl}-1,3-dihydro-5-isobenzofurancarbonitrile;
1-(4-chlorophenyl)-1-{3-(imidazole-1-yl)propyl}-1,3-dihydro-5-isobenzofurancarbonitrile hydrochloride;
1-(4-chlorophenyl)-1-{2-(imidazole-1-yl)ethyl}-1,3-dihydro-5-isobenzofurancarbonitrile;
1-(4-chlorophenyl)-1-{2-(imidazole-1-yl)ethyl}-1,3-dihydro-5-isobenzofurancarbonitrile hydrochloride;
1-(4-chlorophenyl)-1-{3-(pyrazole-1-yl)propyl}-1,3-dihydro-5-isobenzofurancarbonitrile;
1-(4-chlorophenyl)-1-{3-(pyrazole -1-yl)propyl}-1,3-dihydro-5-isobenzofurancarbonitrile hydrochloride;
1-(4-chlorophenyl)-1-{2-(pyrazole-1-yl)ethyl}-1,3-dihydro-5-isobenzofurancarbonitrile; and
1-(4-chlorophenyl)-1-{2-(pyrazole-1-yl)ethyl}-1,3-dihydro-5-isobenzofurancarbonitrile hydrochloride.

16. A pharmaceutical composition comprising the compound represented by Formula 1 or a pharmaceutically acceptable salt thereof according to claim 1 and a pharmaceutically acceptable carrier.

17. A method for treating premature ejaculation, comprising administering to a patient in need of such treatment or prevention a therapeutically effective amount of the compound represented by Formula 1 or a pharmaceutically acceptable salt thereof according to claim 1.

18. A process of preparing the compound represented by Formula 1 according to claim 1 comprising:
   1) preparing a compound of Formula 3 by reacting 5-cyanophthalimide compound of Formula 2 with $R^1$MgBr (step 1);
   2) preparing a compound of Formula 4 by reduction reaction of the compound of Formula 3 (step 2);
   3) preparing a compound of Formula 5 by cyclization reaction of the compound of Formula 4 (step 3);
   4) preparing a compound of Formula 6 by introducing an alkyl group into position 1 of the compound of Formula 5 (step 4);
   5) preparing a compound of Formula 7 by deprotecting the compound of Formula 6 (step 5);
   6) preparing a compound of Formula 8 by reacting the compound of Formula 7 with methanesulfonylchloride (step 6); and 7) preparing a compound of Formula 1 by substitution reaction of the compound of Formula 8 with a R² group and saltation (step 7),
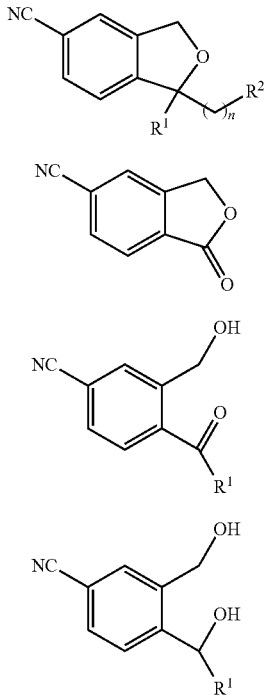
[Formula 1]
[Formula 2]
[Formula 3]
[Formula 4]
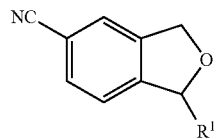
[Formula 5]
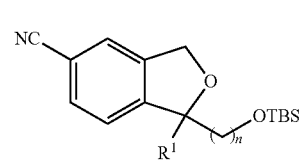
[Formula 6]
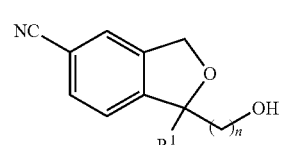
[Formula 7]
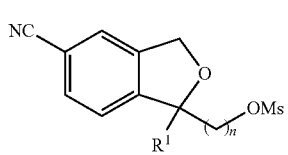
[Formula 8]
wherein, R¹, R², and n are the same as defined in claim 1, and TBS is tert-butyldimethylsilyl.
* * * * *